United States Patent
Ricci et al.

(10) Patent No.: US 8,211,381 B2
(45) Date of Patent: Jul. 3, 2012

(54) DEVICE FOR PERFORMING ANALYSES ON BIOLOGICAL FLUIDS AND RELATED METHOD

(75) Inventors: Antonio Ricci, Siena (IT); Michele Meloni, Siena (IT); Francesco Cocola, Siena (IT)

(73) Assignee: Diesse Diagnostica Senese S.p.A., Milan (IT)

( * ) Notice: Subject to any disclaimer, the term of this patent is extended or adjusted under 35 U.S.C. 154(b) by 1661 days.

(21) Appl. No.: 10/581,964

(22) PCT Filed: Oct. 21, 2004

(86) PCT No.: PCT/IT2004/000575
§ 371 (c)(1),
(2), (4) Date: Jun. 7, 2006

(87) PCT Pub. No.: WO2005/039767
PCT Pub. Date: May 6, 2005

(65) Prior Publication Data
US 2006/0286619 A1    Dec. 21, 2006

(30) Foreign Application Priority Data

Oct. 28, 2003  (IT) ................ FI2003A0273
Feb. 23, 2004  (IT) ................ FI2004A0043

(51) Int. Cl.
*G01N 31/22*  (2006.01)
(52) U.S. Cl. ......... 422/404; 73/864.24; 73/863; 436/47; 422/63; 422/103; 422/104; 422/101

(58) Field of Classification Search ............. 73/863
See application file for complete search history.

(56) References Cited

U.S. PATENT DOCUMENTS

| | | | |
|---|---|---|---|
| 4,187,462 A | | 2/1980 | Haker et al. |
| 4,609,017 A | * | 9/1986 | Coulter et al. .......... 141/1 |
| 4,927,545 A | * | 5/1990 | Roginski ............ 210/745 |
| 5,133,208 A | | 7/1992 | Ricci |
| 5,526,705 A | * | 6/1996 | Skotnikov et al. ....... 73/863 |
| 5,914,272 A | | 6/1999 | Dufresne et al. |
| 6,387,327 B1 | | 5/2002 | Ricci et al. |
| 6,403,328 B1 | | 6/2002 | Clampitt |

(Continued)

FOREIGN PATENT DOCUMENTS

CN        2062448       9/1990

(Continued)

OTHER PUBLICATIONS

Dungan et al. "Sedimentation and dispersion of non-neutrally buoyant Brownian particles in cellular circulatory flows simulating local fluid agitation", Physical Review A, 1988, 38(7):3601-3608.*

*Primary Examiner* — Sally Sakelaris
(74) *Attorney, Agent, or Firm* — McGlew and Tuttle, P.C.

(57) ABSTRACT

A device for measuring the sedimentation rate in biological fluids, and particularly the erythrocyte sedimentation rate in blood samples. The device comprises: holders (3) for test tubes (P) containing samples of biological fluid; agitator devices (25) for agitating the test tubes; at least one detector (17, 19) for reading the levels inside the test tubes. The holders together form a continuous flexible member (1) defining a closed path along which the agitator devices and the detector are arranged.

45 Claims, 16 Drawing Sheets

U.S. PATENT DOCUMENTS

| | | | |
|---|---|---|---|
| 6,520,313 B1 * | 2/2003 | Kaarakainen et al. | 198/369.5 |
| 2003/0087443 A1 | 5/2003 | Pressman et al. | |
| 2003/0113930 A1 | 6/2003 | Winkelman et al. | |

FOREIGN PATENT DOCUMENTS

| | | |
|---|---|---|
| EP | 0391861 | 3/1990 |
| EP | 0898700 | 3/1999 |
| WO | WO91/09295 | 6/1991 |
| WO | WO97/43621 | 11/1997 |
| WO | WO97/43622 | 11/1997 |
| WO | WO98/02726 | 1/1998 |

* cited by examiner

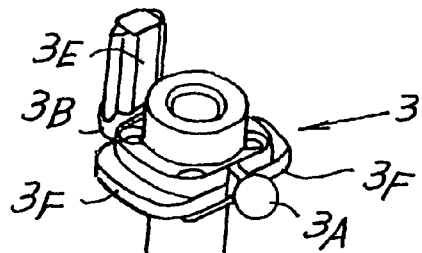
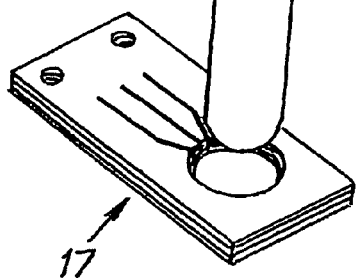
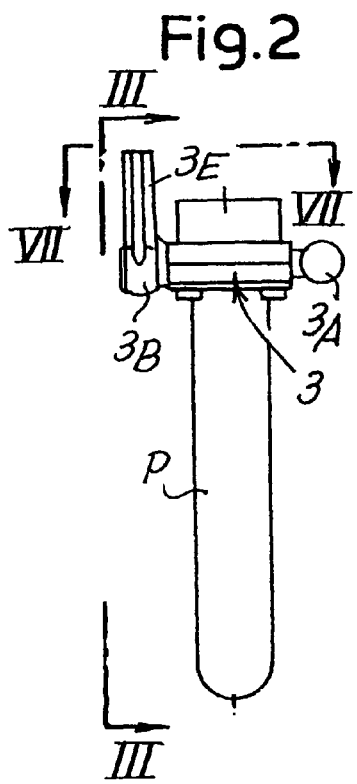
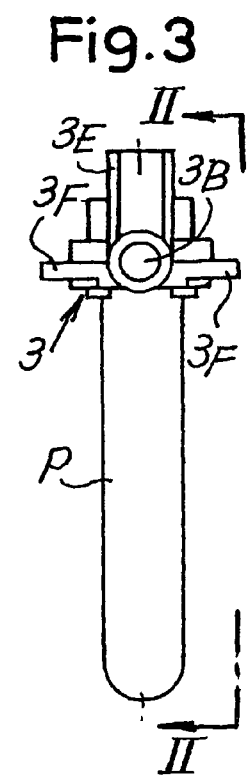
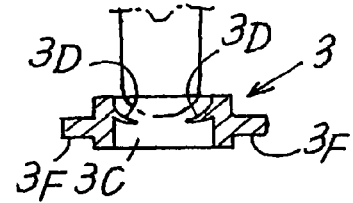
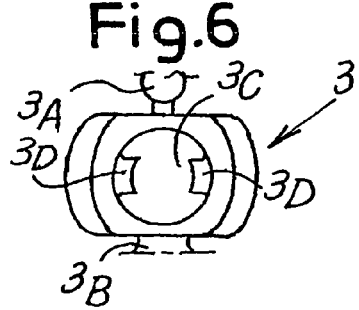
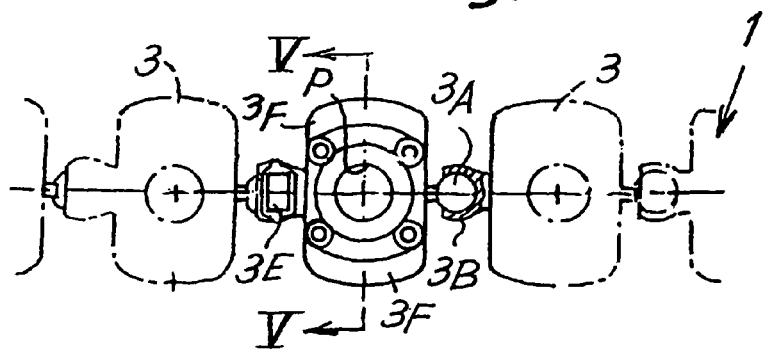

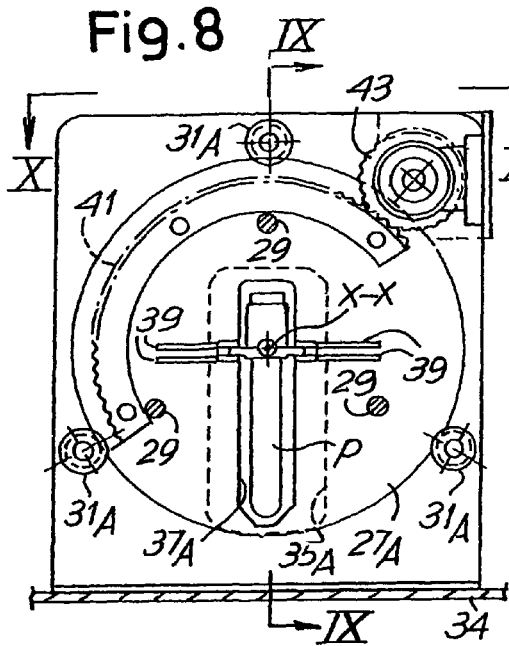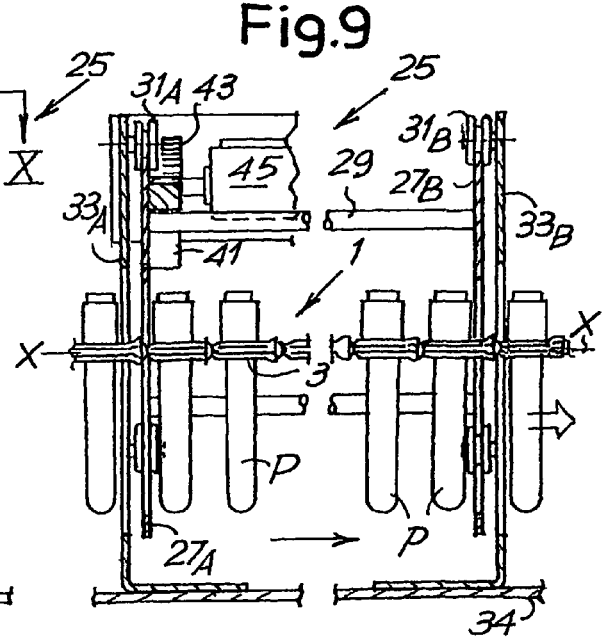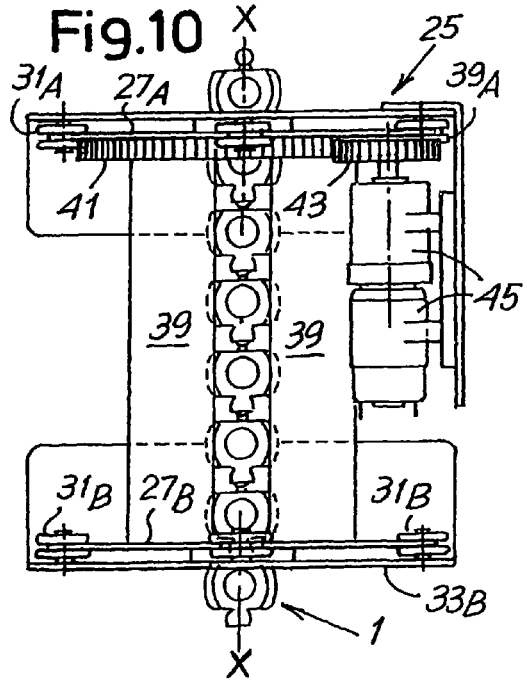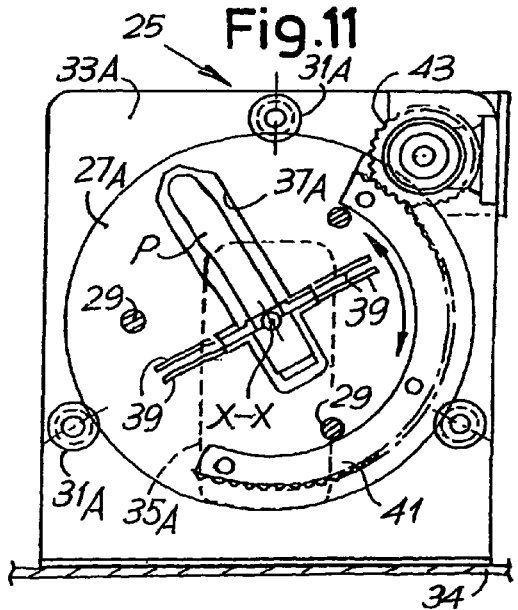

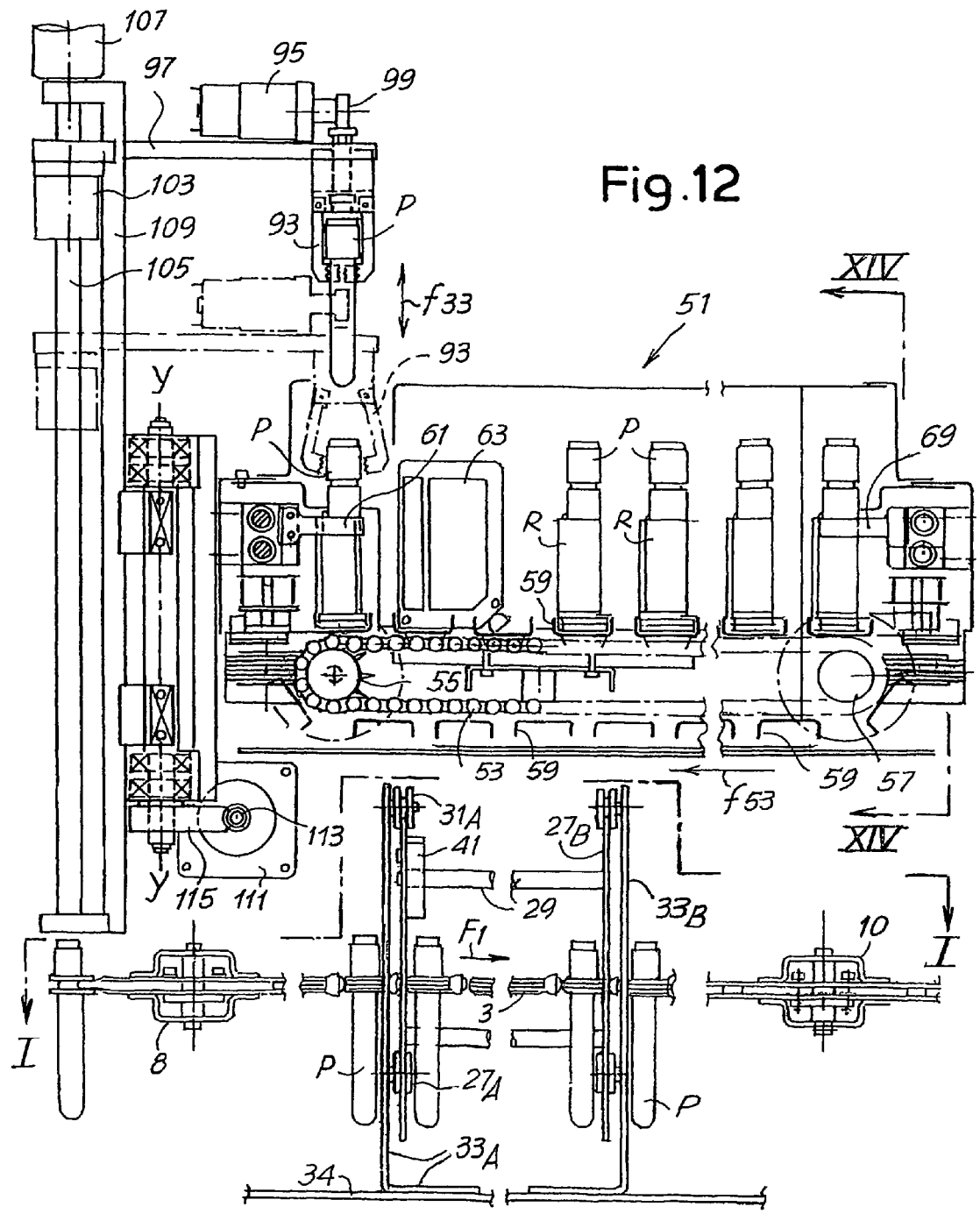

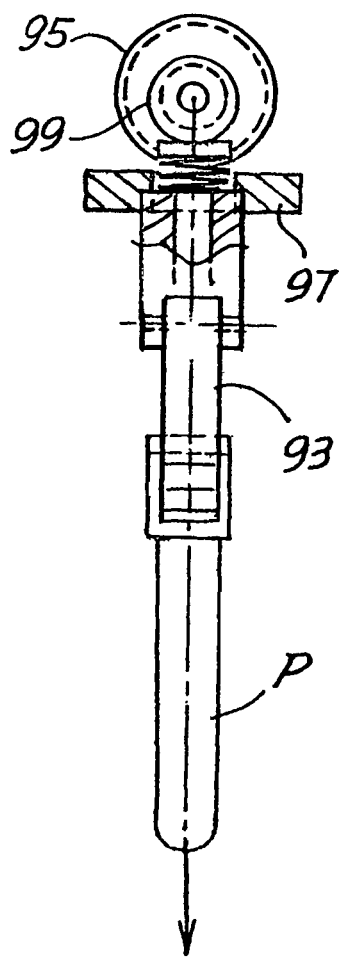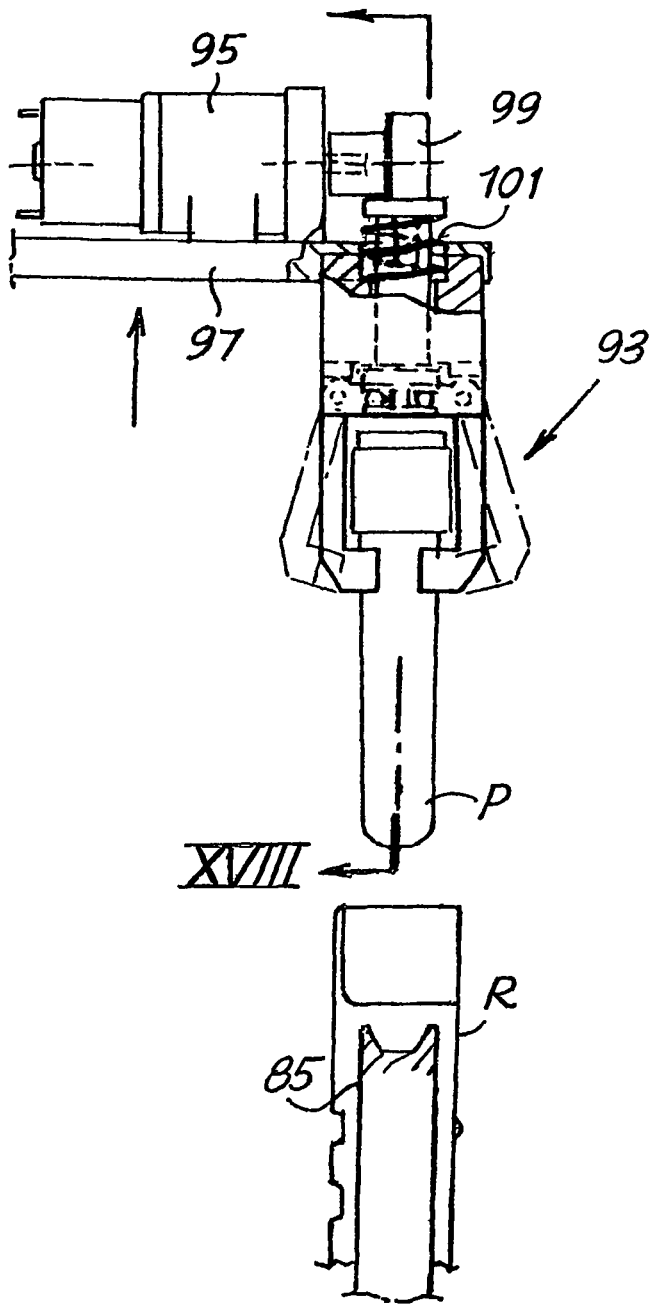

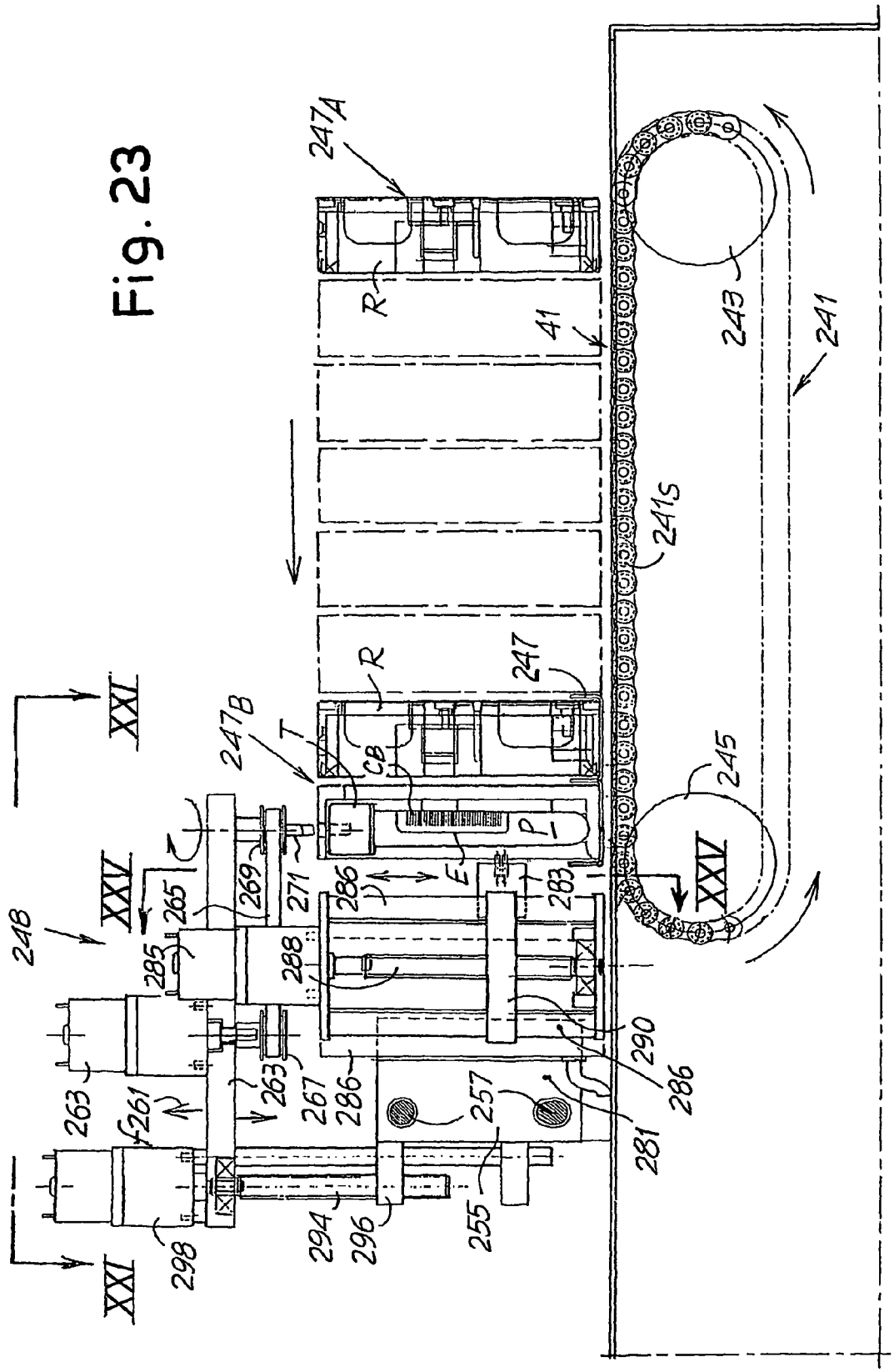

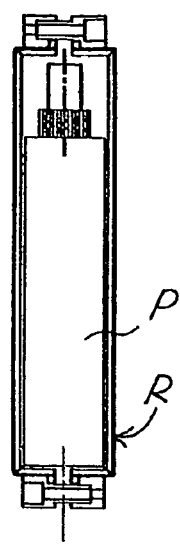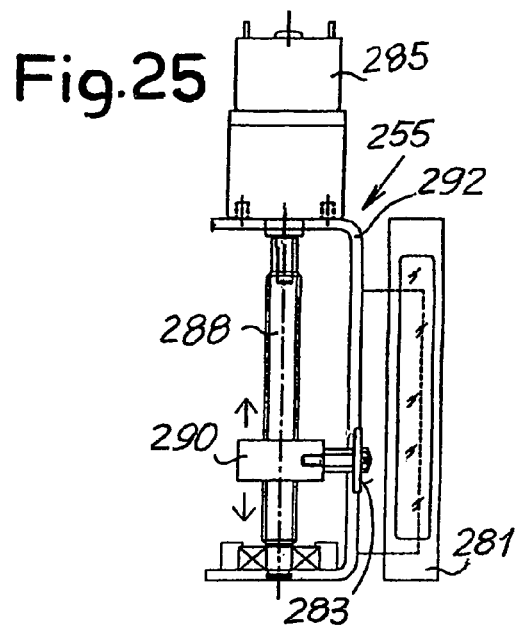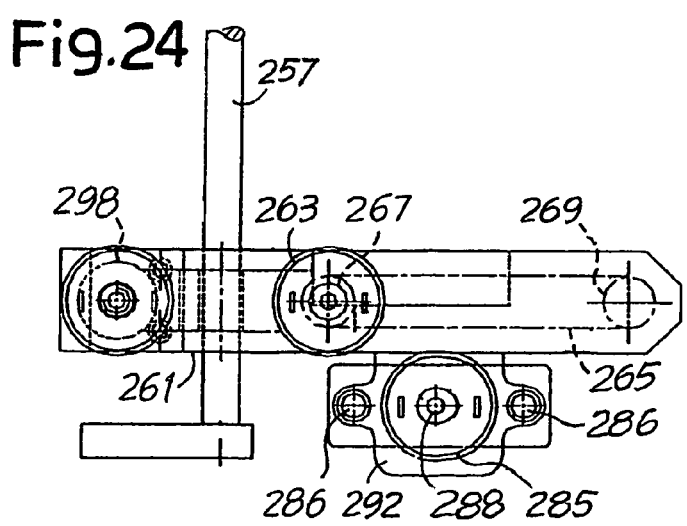

DEVICE FOR PERFORMING ANALYSES ON BIOLOGICAL FLUIDS AND RELATED METHOD

CROSS REFERENCE TO RELATED APPLICATIONS

This application claims the benefit of priority under 35 U.S.C. §119 of FI2003A000273 filed Oct. 28, 2003, the entire contents of which are incorporated herein by reference.

FIELD OF THE INVENTION

The present invention relates to a device or appliance for measuring biological fluids, and particularly for measuring the sedimentation of particles in biological fluids, especially for measuring the erythrocyte sedimentation rate. The invention also relates to a method for taking said measurements.

BACKGROUND OF THE INVENTION

The erythrocyte sedimentation rate is measured as part of the routine analyses performed on blood samples. This analysis can normally be performed using test tubes or cuvettes with a particular shape, suitable for optical reading by means of a transmitter-receiver that slides axially along the test tube. An example of a test tube suitable for this application is described in EP-B-898700. Appliances that use dedicated test tubes to measure erythrocyte sedimentation rate are described in WO-A-9743621 and in U.S. Pat. No. 5,133,208.

Appliances have also been developed that enable the erythrocyte sedimentation rate to be measured using not special test tubes, but the standard test tubes or cuvettes used for complete blood counts (CBC) or similar analyses on blood samples. Such appliances involve aspirating part of the blood sample contained in the cuvette or test tube for CBC into a capillary tube. The erythrocyte sedimentation rate is then measured inside the capillary tube. These appliances offer the advantage of enabling a single type of test tubes to be used for various routine analyses, including the erythrocyte sedimentation rate (ESR). They have considerable drawbacks, however, deriving from the fact that the blood sample must be drawn from the test tube by means of a pipette or capillary tube, which must subsequently be washed or replaced between one test and the next. This involves the production of liquid or solid waste that has to be disposed of, consequently increasing the complexity of the appliance and the corresponding cost of its management, as well as the production costs. Moreover, there is an inherent risk of contamination between the samples analyzed in series.

SUMMARY OF THE INVENTION

An object of the invention is to realize a method for measuring erythrocyte sedimentation rate (ESR) that overcomes or reduces one or more of the drawbacks of the known methods.

Another object of the invention is to realize a new device for measuring ESR.

In particular, an object of the invention is to realize a machine or device capable of performing the analysis using either ESR-dedicated test tubes or standard test tubes of the type generally used for CBC.

Moreover, according to one of its embodiments, an object of the invention is to measure ESR in standard test tubes using any type of rack to contain them during the performance of the blood count.

Substantially, according to a first aspect, the invention relates to a method for performing erythrocyte sedimentation rate analyses, wherein a blood sample is placed in a test tube for CBC, characterized in that, after mixing, said sample is kept in the test tube (the latter preferably being kept in a specific rack) for a predetermined sedimentation time, after which an automatic reading is taken of the sample kept in said test tube and rack, e.g. by a video camera, a capacitive sensor or the like. In essence, the invention involves measuring the ESR in a test tube for CBC without removing the sample from said test tube. When the test tubes are placed in a rack, they can be handled inside the appliance without being taken from the rack. The test tubes, on which various types of test and analysis may be performed, can thus be transferred completely automatically from one appliance to another (including the ESR measuring equipment) without needing to extract each test tube from the rack and without needing to transfer portions of the sample.

According to a particularly advantageous embodiment of the invention, before calculating the erythrocyte sedimentation rate, a check is automatically made by a detection system to establish whether the test tube on which the test is to be performed is a dedicated test tube or a test tube for standard CBC. This enables any correction or correlation of the results of the measurement to be done automatically.

In fact, as any person skilled in the art will know, dedicated test tubes for ESR analyses contain a particular anticoagulant (sodium citrate), different from the anticoagulant used in the test tubes for CBC (called K3EDTA). The two anticoagulants have a different influence on the behavior of the blood sample during sedimentation. The protocol relating to the performance of ESR analyses has been fine-adjusted for it to be done with sodium citrate as 5 the anticoagulant in the blood sample. When the sample contains K3EDTA instead of sodium citrate, its behavior changes and the ESR measurement is thereby affected. Thus, when the erythrocyte sedimentation rate is measured on a sample drawn from a test tube containing K3EDTA as the anticoagulant, it becomes necessary to adopt a specific algorithm to adjust the outcome of the measurement.

Since the method according to the present invention involves measuring the erythrocyte sedimentation rate both in ESR-dedicated test tubes and in CBC-dedicated test tubes, without extracting the sample from the test tube, this can be done on a machine that processes both types of test tube and returns both types of result. Since the anticoagulant contained in the two test tubes is different, it must be possible to automatically or manually set up the procedure for processing the data obtained from the reading of the test tubes in order to take the type of anticoagulant contained in the samples into account. In the preferred embodiment of the method according to the invention, the type of test tube is detected automatically so that the entire measurement procedure can be automated without the operator needing to take action to specify the type of calculation to perform on the data obtained depending on the type of test tube used.

According to a different aspect, the invention involves a method for measuring the erythrocyte sedimentation rate in a blood sample contained in a test tube, wherein: the sample is kept in the test tube for a predetermined time after adequate mixing; an automatic detection system ascertains the type of test tube wherein the sample is contained; the reading of the erythrocyte sedimentation rate is subsequently taken by means of an automatic reading system, the recorded value being processed according to the type of test tube containing the sample.

According to yet another aspect, the invention relates to a device for performing analyses on the erythrocyte sedimentation rate in blood samples contained inside test tubes, comprising a control unit and a system for reading the test tubes containing the sample on which to perform the analyses. Characteristically, the reading system takes the reading of the sample inside the respective test tube without extracting the sample from the tube, irrespective of the type of test tube wherein said sample is contained and without removing said test tube from the specific rack in which it has been placed.

According to an advantageous embodiment of the invention, the device involves the control unit having detection means for automatically recognizing the type of test tube wherein the samples to analyze are contained. For instance, the detection means may comprise a video camera that also constitutes the sample reading system. By means of a suitable image-processing software, the video camera can be used on the one hand to view and interpret the content of the test tube, determining the erythrocyte sedimentation rate of the sample, and on the other to distinguish one type of test tube from the other. It is known, in fact, that ESR-dedicated test tubes have a different shape from the test tubes for CBC. The different image captured by the video camera can be processed by the image-processing to distinguish one type of test tube from the other.

Alternatively, arrangements can be made to associate the test tubes with a transponder and to provide detection means, interfaced with the control unit of the analyzer, which interrogate the transponder. Data contained in the transponder enable the system to recognize the type of test tube loaded each time in the analyzer.

In an advantageous embodiment of the invention, the device also includes means for reading a bar code or other machine-readable code (for instance, wording with OCR characters) attached to the test-tube. The bar code, or other machine-readable code, contains the data for identifying the person to whom the sample contained in the test tube belongs, in addition to data useful for performing the analyses. In particular, since the device and the method according to the invention enable test tubes for CBC to be used to measure the ESR, it is advantageous to provide for the information contained in the bar code (or similar code) to include information that informs the device whether or not a given test tube has to undergo ESR analysis. In fact, the test tubes for CBC may contain samples requiring testing only for the CBC and not for the ESR as well, in which case the device can skip the test tube on which the ESR measurement is not required and proceed with the analysis of the next test tube.

When the sample reading system provides for the use of a video camera, the bar code (or similar code) attached to the test tubes can be read by said appliance. Vice versa, arrangements can be made for the erythrocyte sedimentation rate to be read by another type of sensor, e.g. using capacitive sensors, nephelometric optics, infrared optics, or non-optic ultrasound. In this case, the sensor for reading the ESR will be associated with a bar code reader, such as a normal laser scanner or a CCD for reading bar codes. Other types of reader can be used for other types of machine-readable code, even using a magnetic reading, for instance, instead of an optical reading.

To be able to take the reading of the CBC test tubes, to which labels can be attached to provide various details relating to the content of the test tube (particularly when the reading system comprises a video camera), it is advisable to equip the appliance with a mechanism for rotating the test tubes containing the samples to analyze in order to orient the test tube correctly in relation to the reading system (by turning it around its own axis). Said orientation can serve the usual purpose of presenting a free area of test tube to the sample reading system and/or of presenting the system for reading the bar code (or other code that can be read by the system) with the label containing the information the system needs to read in order to perform the analysis correctly and associate the result with the patient whose sample is contained in the test tube in question.

When the sample is read by a capacitive sensor, ultrasound or infrared device, the angular orientation of the test tube may serve simply to present the label in front of the reader to enable it to be read, while the erythrocyte sedimentation rate can even be read through the label, since the capacitive sensor is unaffected by its presence.

In an advantageous embodiment, the device according to the invention comprises a magazine for holding and agitating a plurality of test tubes, a sedimentation zone wherein the test tubes are left in a vertical or tilted position to allow for the sedimentation of the sample, and a test-tube reading area, wherein the reading system is installed. In the reading area, after a predetermined sedimentation time, the height of the line separating the plasma from the blood cells is measured and compared with the total height of the sample. The erythrocyte sedimentation rate is calculated in a known manner from this information, which can be recorded by a video camera optical system, or by any other reading system, e.g. of capacitive type, as mentioned earlier.

According to an embodiment of the invention, the magazine advantageously comprises a first flexible conveyor with associated seats for engaging and retaining racks containing test tubes, which are compatible with all available types of rack for CBC instruments or otherwise. This flexible conveyor is realized and arranged so as to make the seats for holding the racks containing the test tubes transit sequentially in the following positions: a rack-loading position, a position for transferring the racks to the sedimentation area, a position for receiving the racks from the reading area after the reading of the samples, and a position for ejecting the processed racks.

Advantageously, the conveyor forming the magazine moves along a closed path lying on a substantially vertical plane. The movement of the test tubes held in the magazine thus configured induces the agitation of the samples, which is thus done inside the analyzer.

In a possible embodiment, the device includes a tray supporting the racks of test tubes to process, wherein the latter lie, for instance, horizontally. A plunger is provided to individually collect the single racks of test tubes in the magazine.

In another possible embodiment of the device according to the invention, there is a second flexible conveyor, complete with a plurality of seats for racks containing the test tubes to process, in the sedimentation area. This second flexible conveyor advances in steps to bring single racks to the reading area from where they are picked up from the magazine. The time it takes for this transfer is advantageously the same as the sedimentation time, so that when they reach the reading area, the test tubes can undergo the erythrocyte sedimentation rate measurement. Feasibly, a part of the sedimentation time may also be spent by the test tubes when they are in the magazine.

According to an advantageous embodiment, the second conveyor provided in the sedimentation area has a substantially horizontal stretch of straight path extending between the position where the racks are received from the magazine and a reading position. This stretch of straight path is situated substantially at the same height as a corresponding horizontal stretch of the conveyor forming the magazine. In this way, the racks containing the test tubes can be transferred from one conveyor to the other by a simple plunger.

The structural and functional features of the device according to the invention described and illustrated herein can also be advantageously achieved in a device that measures the ESR only in dedicated test tubes. In this case, however, it is unnecessary to be able to recognize the type of test tube presented for reading and/or to be able to specify processing parameters for the data recorded as a function of the type of test tube, and of the type of anticoagulant contained therein.

According to a different aspect of the invention, a device is provided for measuring the sedimentation rate in biological liquids, and especially the rate of erythrocyte sedimentation in blood samples, comprising: holders for test tubes containing samples of biological fluids; agitator devices for agitating said test tubes; at least one detector for reading the levels of sample and/or sediment inside said test tubes; characterized in that the holders are provided in a continuous flexible member defining a closed path along which the agitator devices and said at least one detector are arranged.

As will appear clear from the following description, an apparatus of this type can be used to insert single test tubes (even the generic test tubes used for complete blood counts) in respective holders in the flexible member, which moves the test tubes along a path on which they are agitated, held in position to allow for sedimentation and submitted to one or more readings.

In an advantageous embodiment, along the closed path defined by the flexible member there are: at least one agitating area, wherein said agitator devices are installed; at least one sedimentation area; and at least one reading area, wherein the detector is installed. In practical terms, at least two detectors will be provided to perform a first reading to determine the level of the sample after agitation and a second reading to determine the level of the sediment in the sample after sedimentation. There may also be several subsequent readings at predetermined spatial distances and consequently—since the advancement rate of the flexible member is known—at determined time intervals. The level of the sample in the test tube may also be determined outside the appliance, or the same detector may perform the two readings, in which case it is sufficient to have one detector to take the measurements. However, also for the purposes of the automation of the analytical process, it is advantageous and preferable to provide at least one detector downstream from the agitation area and at least one second detector downstream from the sedimentation area.

The flexible member preferably defines a path lying on a substantially horizontal plane, so that the test tubes or cuvettes come to be in a substantially vertical position during the sedimentation and reading phase. They may be slightly tilted with respect to the vertical, however.

In a practical and advantageous embodiment, the holders formed by the continuous flexible member are composed of interlocking elements that form a flexible chain member, e.g. by means of spherical articulated joints that allow for the ample movement of one element with respect to another, with the opportunity to remove a single test tube from the plane on which the continuous flexible member lies, to ensure an effective agitation of the sample.

The various elements forming the flexible member may each contain one or more seats for one or more test tubes. Preferably, for the sake of simplicity of construction and automation of the appliance, each element shall comprise a single seat for a single test tube.

In an advantageous embodiment of the invention, the agitator devices are designed and constructed to induce an oscillation of the holders forming the flexible member and designed to hold the single test tubes.

Advantageously, the agitator devices are designed and arranged so as to induce the oscillation of said holders (forming the continuous flexible chain member) outside the plane on which the flexible member lies, so as to make the axis of single test tubes oscillate with respect to the direction orthogonal to said plane.

In a particularly advantageous embodiment of the invention, the agitator devices include guides wherein the holders forming the continuous flexible member are engaged, and said guides cause the oscillation of said holders. The holders forming the continuous flexible member include elements for engaging them to said guides, e.g. in the form of sliding shoes.

In a possible embodiment, the agitator devices comprise fixed guides extending along at least a portion of the path defined by the flexible member, which are made and arranged so that the holders that transit along said guides are forced to oscillate outside the plane on which said continuous flexible member lies as it advances. In practical terms, these guides may be helical in shape and, as the flexible member advances, cause the rotation through 360° of each holder in the flexible member around an axis parallel to the direction in which the flexible member advances in the agitating area, i.e. parallel to the axis of the helix formed by the guides.

To obtain a more effective agitation, however, it is preferable for the guides engaging the holders forming the flexible member and forming part of the agitator devices to be mobile guides extending along a portion of the path defined by the flexible member. In this case, the guides are made and arranged so that their movement induces the oscillation of the holders connected thereto outside the plane on which the continuous flexible member lies. The oscillating movement imposed by the guides (provided with their own actuator, for instance) is thus unrestricted by and independent of the forward feed of the flexible member carrying the test tubes.

For example, the agitator devices can comprise a rotor coaxial to a stretch of the path covered by the flexible member and presenting elements, in the form of guides or the like, for engaging the holders that come into line with said stretch along the path of the flexible member. The rotor has a rotating and/or oscillating movement around its own axis, which induces the oscillation of all the elements and consequently of the respective seats or holders and test tubes engaged to said rotor with respect to the remaining portion of the flexible member not engaged thereto. Thus each test tube, while remaining in its holder and completing the entire closed path defined by the continuous flexible member, can be agitated and then left to rest in a vertical position (or possibly even tilting with respect to the vertical but at a fixed angle) to complete the sedimentation phase and the reading of the levels in said test tube.

Outside the agitating area, there may be fixed guides to avoid any vibration or accidental oscillation of the test tubes.

To achieve a reliable control of the device, according to an improved embodiment of the invention, the continuous flexible member includes a transponder associated with each test-tube holder. The transponder contains data that enable the recognition of each holder associated with a given test tube, which in turn is marked with information, attached by means of a label with a barcode, for instance, or other preferably machine-readable code, e.g. using an OCR reading system. A control unit associates the data in each transponder with the data on the test tube inserted in the respective holder. With a system for scanning the transponders in one or more suitable places along the path of the flexible member, it is consequently possible to identify the position of each test tube. The device thus becomes extremely reliable and error-free, even in the event of a temporary power failure, which might make the stepwise control system lose track of the position of the various test tubes along the path covered by the flexible member.

The test tubes can be manually inserted in and withdrawn from the holders formed by the flexible member. However, along the closed path defined by the flexible member there will preferably be at least one extractor for removing the test tubes from the holders. In a preferred embodiment of the invention, there will be two extractors, for purposes that will be further explained below.

In a straightforward, not completely automated embodiment of the device, there can be an operator to place individual test tubes in the various seats in the holders, after making the control unit acquire the information attached to each test tube.

However, the appliance can be further developed and improved by providing automatic manipulators for automatically inserting the test tubes in the holders after automatically reading the information attached to the test tubes. These manipulators may, for instance, be arranged and designed to collect single test tubes from a rack of test tubes and to insert them in respective holders. These manipulators may be arranged in a setup unit for preparing the test tubes, which is advantageously and preferably placed above the continuous flexible member and the means for agitating and reading the sedimentation rate.

In a possible embodiment of the invention, the setup unit includes a scanner station for automatically reading labels applied to the test tubes and for ascertaining for each tube whether the sedimentation rate has to be measured on the sample it contains. Moreover, mechanisms can be provided for extracting single test tubes from the respective racks and transferring and inserting them in the holders in the continuous flexible member underneath.

According to still a different aspect, the invention relates to a method for measuring the sedimentation rate in biological fluids, and especially the erythrocyte sedimentation rate in blood samples, comprising: an agitation step of the test tubes containing samples of said biological fluids; a sedimentation step of said samples; and reading step of the level of sediment in said test tubes; characterized by: inserting said tubes in respective holders forming a continuous flexible member; advancing said continuous flexible member along a closed path; and subjecting the single test tubes, as they move along said closed path, to said agitation, sedimentation and reading steps in areas sequentially arranged alongside said closed path.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIGS. 2 to 7 show details of one of the holders comprising the flexible member and of the way in which the test tubes are inserted and retained therein;

FIG. 8 shows a cross-section through VIII-VIII of FIG. 1 of the agitator devices;

FIG. 9 shows a cross-section through IX-IX of FIG. 8;

FIG. 10 shows a plan along the line X-X of FIG. 8;

FIG. 11 shows a similar cross-section to the one in FIG. 8, but in a different angular position of the test tubes engaged by the agitator devices;

FIG. 12 shows a cross-section through a vertical plane of the complete setup unit installed above the continuous flexible member;

FIGS. 17 and 18 show details of the device for transferring the test tubes from the setup unit to the flexible member underneath, FIG. 18 being a view along the line XVIII-XVIII of FIG. 17.

FIG. 21A is a seat in the magazine;

FIG. 23 is a side view along the line XXIII-XXIII of FIG. 22;

FIG. 24 is a local plan along the line XXIV-XXIV FIG. 23;

FIG. 25 is a local view along the line XXV-XXV of FIG. 24;

DESCRIPTION OF THE PREFERRED EMBODIMENTS

Figure 1:
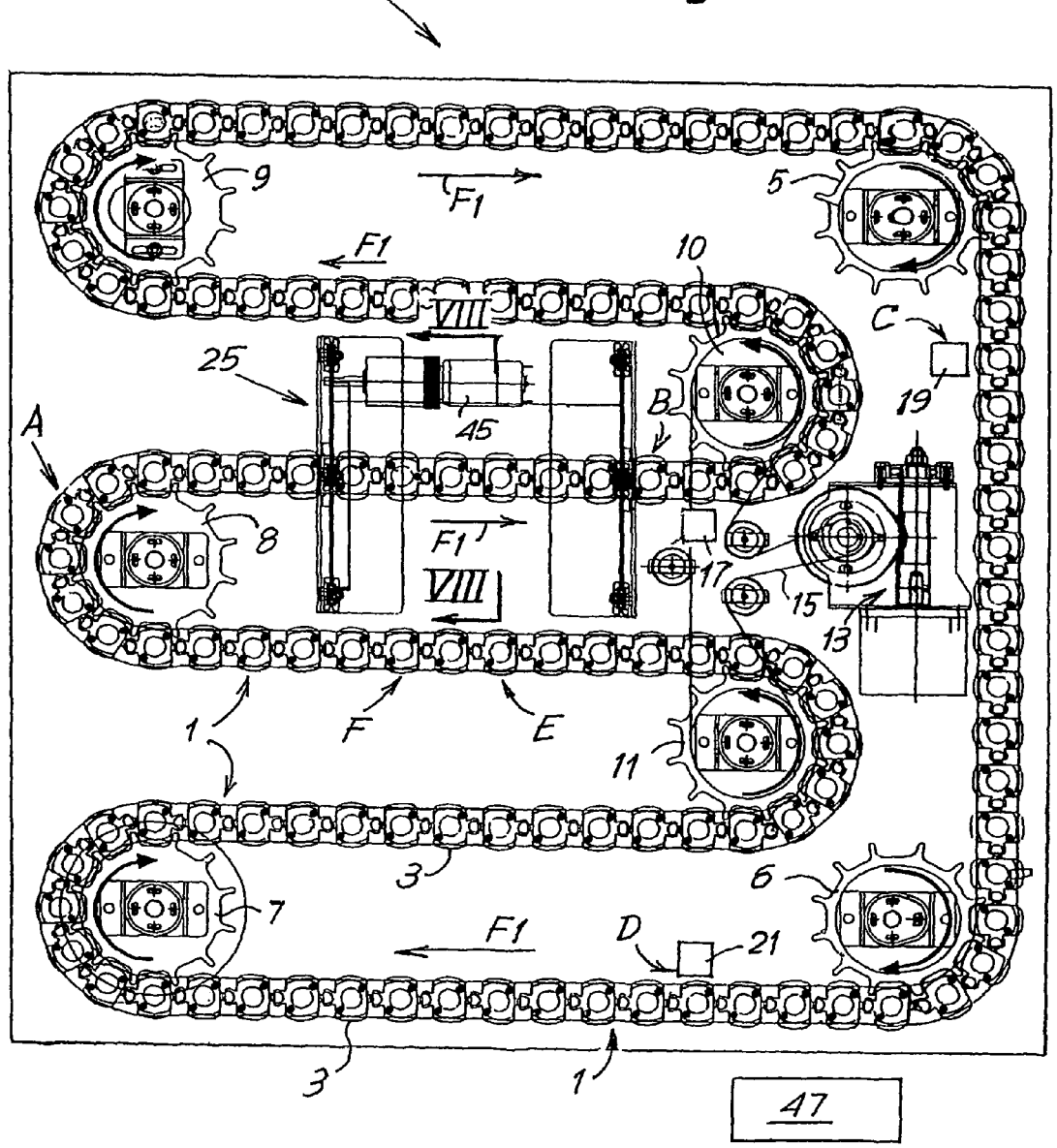
FIG. 1 shows a plan along the line 1-1 of FIG. 12 of the flexible member with its path and the elements and devices provided along said path.

Referring to the drawings in particular, FIGS. 1 through 18 the first embodiment, the device comprises two sections or units: the agitation, sedimentation and reading section or unit, comprising the flexible member with the holders for the test tubes, and a section or unit installed over it hereinafter called the setup unit. The latter could be omitted in the case of a more economical, less automated device. In the following paragraphs, the unit underneath, with the agitation, sedimentation and reading elements, is described first, followed by the optional setup unit with the respective means for transferring the test tubes.

Referring initially to FIGS. 1 to 11, the lower unit in the device, globally indicated by the numeral 2, comprises a flexible member composed of a chain formed by a series of single elements 3 that will be described in detail with reference to FIGS. 2 to 7. Each element 3 has a seat or holder for a respective test tube P, such that a plurality of test tubes can be made to advance along a closed path covered by the flexible member 1.

Said path is defined by seven drive wheels 5, 6, 7, 8, 9, 10 and 11, of which wheels 5 to 9 are idle, while wheels 10 and 11 are motorized by means of a geared motor 13, controlled electronically by a central unit, and a toothed belt 15, lying underneath the plane on which the flexible member 1 lies. The geared motor 13 induces a stepping forward feed of the flexible member 1, each step corresponding to one element 3. Subsequent steps are taken at an adjustable time interval for purposes that will be further explained below.

Six positions along the path of the flexible member 1 are identified in FIG. 1 by the letters A, B, C, D, E, F for the functions and purposes described below.

Position A is where the single test tubes P are inserted in the holders in the elements 3 as the latter transit through said position.

In position B there is a first detector, generically indicated by the numeral 17, that can be a capacitive sensor, a video camera, an optical system with a transmitter and receiver, or any other suitable detector for determining the level of the sample contained in each test tube P transiting in the position B.

In positions C and D there are respectively a second and a third detector, indicated by the numerals 19 and 21, that can be of the same type as the detector 17, or they can also be of a different type. They serve to determine the level of the sediment in the samples after the test tubes have been kept in conditions suitable for sedimentation for a predetermined time. The two detectors 19 and 21 occupy different positions along the path of the flexible member 1, so that they take a similar reading at two different time intervals. The detector 21 may also be omitted.

In the positions E and F there are two extractors (not illustrated), that take the test tubes out of the holders 3 and unload them into two different 15 containers. An electronic control programs the device so that all the test tubes that have been measured correctly by the detectors 17 and 19, and the optional detector 21, are unloaded by one of the two extractors into a first container. Vice versa, the test tubes that have prompted an error (e.g. because that were found empty, illegible or for some reason prevented the analysis from being completed) are unloaded by the other extractor into the second container. This enables the operator to identify the samples easily and thus also the patients whose analyses must be repeated.

The shape of the elements 3 forming the flexible member 1 is shown in detail in FIGS. 2 to 7. In practical terms, each element 3 is a link in a chain, and is complete with male-female spherical joints in order to be attached to the previous and subsequent elements. The male spherical element in the joint is indicated by the numeral 3A and the female spherical element is indicated by the numeral 3B.

The body of the element 3 has an open-bottomed seat 3C (FIGS. 5, 6), wherein the test tubes P are inserted. There are two flexible retainer tabs in the open-bottomed seat 3C, indicated by the numeral 3D. Solidly attached to the female portion 3B of the spherical joint there is a seat 3E wherein a transponder is inserted, so that each test tube is associated with a transponder for the purposes clarified below. Moreover, the body of each element 3 includes two sliding shoes 3F for engaging in and sliding along guides arranged along the path of the flexible member. Said guides can extend along the entire path to avoid any unwanted oscillation of the single holders 3, especially in the area intended for the sedimentation of the samples. A part of the guides, vice versa, can be movable to induce the oscillation of the holders and the consequent agitation of the samples of blood or other biological fluid contained in the test tubes. Each holder 3 can be made from a simple synthetic resin molding.

FIG. 4 also schematically illustrates a detector of the capacitive type, indicated by the numeral 17, that can be used in the various places along the path of the flexible member. Said detector is made to transit along the length of the test tube, from the bottom to the area underneath the holder 3, in order to read the level of the sample and/or of the sediment. After completing the reading, the detector moves down again out of the test tube's path to enable it to be carried forward by the flexible member 1. As mentioned earlier, this is just one of the types of detector that can be used in this type of device, not the only one. Generally speaking, the device can be fitted with one or more, even different, types of detector, providing they are suitable for providing the information for the reading of which the device is designed.

In the straight stretch of the flexible member 1 coming between the idle wheel 8 and the motorized wheel 10, there are agitator devices, generically indicated by the numeral 25 and illustrated in greater detail in FIGS. 8 to 11.

The agitator devices comprise a rotor composed of a pair of discs 27A, 27B, joined together by connection bars 29 (omitted for the sake of clarity in FIG. 10). The discs 27A and 27B are supported revolvingly around an axis coinciding with the axis X-X of the spherical joints linking the elements 3 in the portion of flexible member 1 that transits through said discs 27A, 27B.

Each disc holder is composed of a set of three grooved wheels 31A, 31B idlingly supported on respective bearing plates 33A, 33B attached to the base 34 of the device and extending orthogonally to the plane on which the flexible member 1 lies. Each plate 33A, 33B has a slot 35A, 35B for the passage of the test tubes and the flexible member 1, and a similar passage 37A, 37B is provided in the two discs 27A, 27B. Solidly attached to the two discs 27A, 27B, there are guides 39 that extend parallel to the axis X-X of oscillation of the rotor formed by said discs and on either side of said axis. Each guide is comprised of a pair of parallel separate blades, rigidly attached to the two discs 27A, 27B. The sliding shoes 3F of the single holders 3 forming the flexible member 1 are inserted and slide between the two pairs of blades (FIG. 7). A toothed crown sector 41, engaged with a pinion 43 driven by an electric motor 45 is solidly attached to the disk 27A.

The agitator devices 25 hitherto described operate as follows: the continuous flexible member 1 advances stepwise along its path. At each instant a certain number of holders 3 (six in the example illustrated in FIGS. 9 and 10) are engaged in the guides 39 of the rotor formed by the discs 27A, 27B. The oscillating movement imposed by the motor 45 on the rotor, by means of the pinion 43 and the sector 41 of toothed crown, induces an oscillation of the holders 3 engaged in the guides 39 and consequently of the test tubes P inserted in said holders. FIGS. 8 and 11 show the two extreme positions occupied by the test tubes P during said oscillation. The spherical joints between the elements 3 enable each holder to rotate with respect to the previous one and the following one in order to come out from the plane on which the flexible member 1 lies. Thus, between one forward feed step of the flexible member 1 and the next, the test tubes inserted in the six holders 3 engaged to the rotor by means of the guides 39 can oscillate freely around the axis X-X, without being obstructed in said oscillation by the holders 3 immediately upstream and downstream from the discs 27A, 27B (with respect to the forward feed direction F1 of the flexible member 1).

The oscillating movement imposed by the motor 45 is separated from the stepping forward feed motion of the flexible member 1 and can have any frequency suitable for ensuring the necessary agitation of the test tubes P. In this way, each test tube P that moves forward being supported the flexible member 1 is agitated for a period of time coinciding with the time it stays between the two discs 27A, 27B, i.e. a multiple of the time taken for each forward feed step, said multiple corresponding to the number of holders 3 simultaneously coming between the discs 27A, 27B, i.e. six in the example illustrated. Preferably the oscillation stops briefly during the forward feed movement of the flexible member composed of the holders 3, but said stoppage in the oscillation is very short-lived, since the stoppage between one step and the next lasts substantially longer than the time it takes to complete each forward feed step.

The detector 17 situated immediately downstream from the agitating area defined by the agitator devices 25 reads the level of the sample contained in each test tube before the sedimentation phase.

The path covered by the flexible member between the outlet from the agitator devices 25 and the second detector 19 in position C constitutes the sedimentation area. Along this path, each test tube remains in the vertical position throughout the time it takes to pass from position B to position C. The sedimentation time is defined by the pertinent standard recommendations for the analyses to perform. The distance between positions B and C, and the time it takes to complete each step plus the stoppage between one step and the next are predetermined so as to ensure that each test tube substantially takes the necessary sedimentation time to transit from position B to position C, naturally bearing in mind the time it takes to complete all the necessary procedures on each test tube in the various places along the path of the flexible member 1, e.g.: the procedure for inserting the test tube in position A; the readings taken in positions B and C, and possibly also D; the withdrawal and unloading of the test tubes in positions E or F.

The reading of the height of the sediment in the sample contained in each test tube is taken in position C by the detector 19. The data recorded by 25 the two detectors enables the calculation of the erythrocyte sedimentation rate (ESR).

The third detector 21 (if any) in position D is placed at a distance from the detector 19 sufficient to enable each test tube P to settle further for a given amount of time as it passes from position C to position D. This third detector 21 thus takes a second reading of the level of the sediment after a second time interval.

The test tubes are then fed forward from position D to position E or F for unloading, by means of an ejector that can be made in a manner briefly described below.

Along the forward feed path of the member 3, there may be fixed guides (with the exception of the area occupied by the agitator devices 25) to keep the test tubes constantly oriented, preferably in a vertical position. These guides can be made in much the same way as the guides 39 of the rotor forming part of the agitator devices 25.

The motors 13 and 45, and the detectors 17, 19 and 21, and also the ejectors (not illustrated) in positions E and F, are all interfaced with a programmable control unit, schematically indicated by the numeral 47. Said unit controls and coordinates the movement of the various parts of the device, it acquires the data from the readings made by the detectors and it also acquires, for instance by means of a barcode reader, the information applied to each test tube. Said barcode reader (or other suitable interface) can be provided on a handpiece for use by the operator who takes action, in the more straightforward embodiment, to load each test tube in the various holders that transit through position A, so that the programmable system can acquire the details on the patient with whom the outcome of the analyses performed by the device must subsequently be associated.

As described later on, these procedures can be automated by using a setup unit installed over the continuous flexible member 1.

Along the path of the flexible member 1 there are one or more transponder scanners of known type (not illustrated). For example, one of these can be placed in position A and one or more of them can be placed in other suitable positions, even coinciding with positions B, C, D, E, F, or in between them.

Thus, each time a holder 3 transits in position A, the central unit 47 not only acquires the information applied to the test tube inserted in said holder, it also associates a specific transponder with the given test tube. This enables the system to know the position of each test tube at all times, even in the event of a temporary power failure, without relying exclusively on the counter of the forward feed steps imposed by the motor 13 for said information.

The setup unit which can be associated with the above-described device is illustrated in the Figures from 12 onwards and indicated globally by the numeral 51. It comprises a first continuous conveyor 53 driven around wheels 55, 57 and fitted with a series of seats 59 which may also be interchangeable, for housing racks R containing test tubes P. The racks R can be of various shapes and types and this may make it necessary to change the seats 59, depending on the racks used by a given laboratory.

Figure 13:
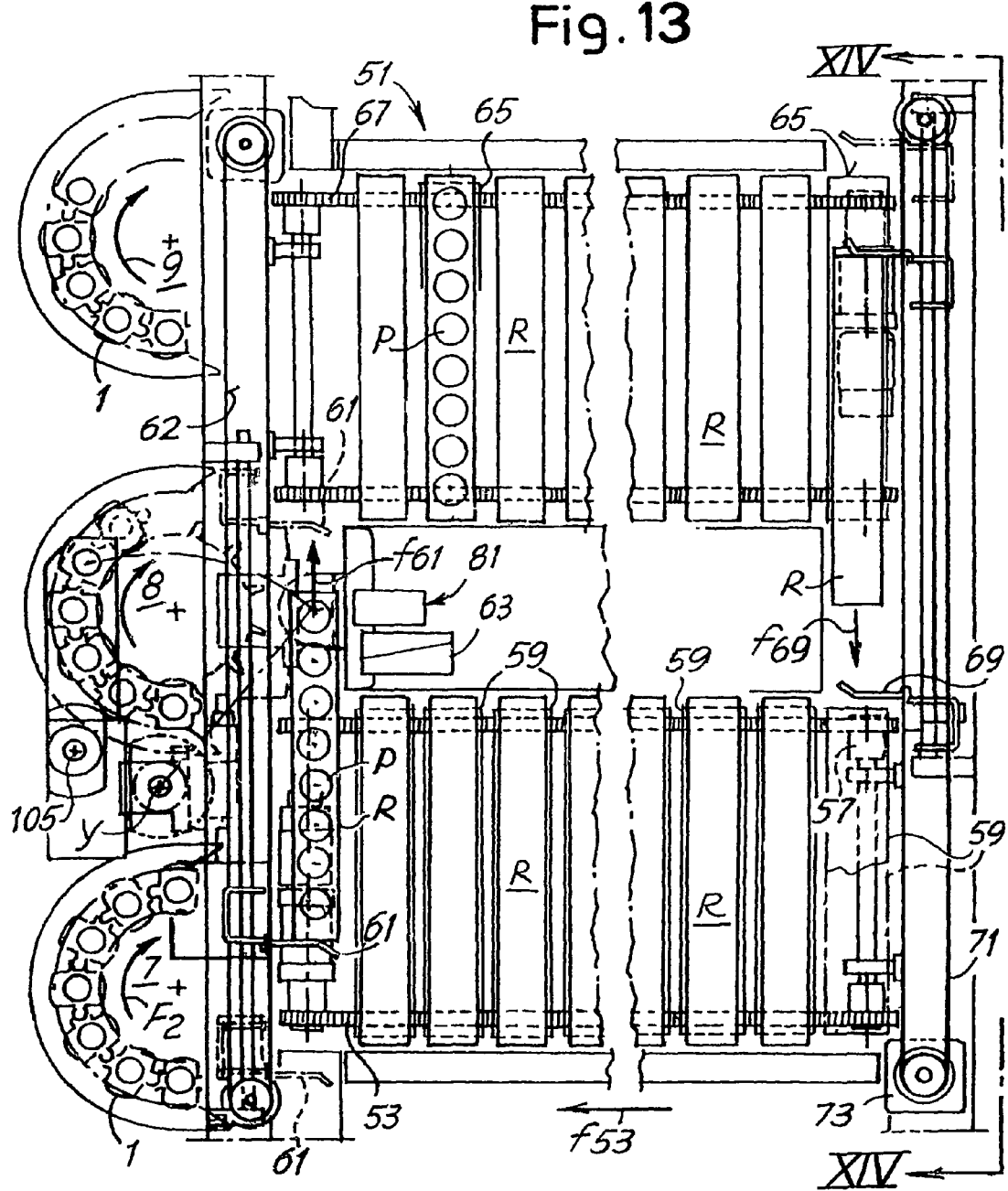
FIG. 13 shows a plan of the complete setup unit.
Figure 14:
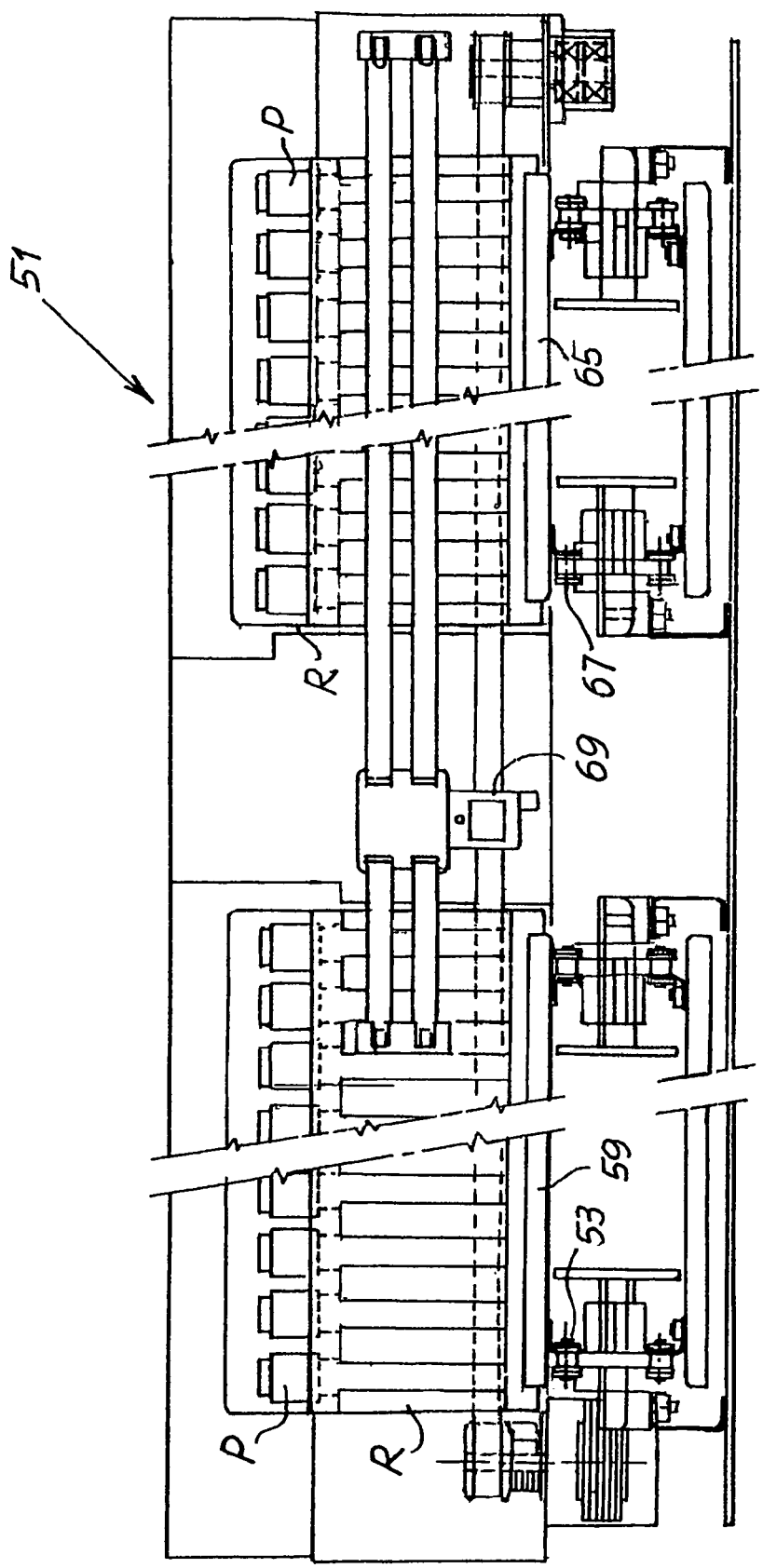
FIG. 14 shows a rear view along the line XIV-XIV of FIGS. 12 and 13.

The movement of the conveyor 53 (arrow f53) transfers each seat 59 with its respective rack R from a loading area to a collection area, shown in FIGS. 12 and 13 at the left-hand end of the path covered by the conveyor 53. Here, a first transfer device 61 pushes each rack in the direction of the arrow f61 to make it transit in front of a barcode reader 63, or other device for reading the information attached (with a printed label or other means) to each test tube contained in the rack. The transfer device 61 is driven by a motor, controlled by the unit 47, by means of a belt 62 or other mechanical drive element As it transits in front of the barcode reader 63, the latter determines whether each test tube must undergo erythrocyte sedimentation rate measurement. In fact, not all the samples contained in the various test tubes in the racks R will necessarily require said test. There may also be some samples that only require other analyses, e.g. a complete blood count.

The forward feed of the rack in the direction of the arrow f61 is done stepwise to allow for the reading of the single labels on the one hand, and on the other for the collection and transfer of the single test tubes from the rack R to the flexible member 1 underneath, for the ESR measurement. The test tubes that do not need to undergo ESR measurement remain in the rack R and are pushed, together with the rack, by the same transfer device 61 into a corresponding seat 65 on a second conveyor 67, substantially mirroring the conveyor 53.

This second conveyor 67 serves as the interface with the operator, who inserts racks to process in the seats 65 in said conveyor and removes racks already processed from said seats. The transfer of the racks inserted by the operator in the seats 65 from said seats to the seats 59 in the first conveyor 53 is done by a second transfer device 69 substantially mirroring the transfer device 61 and driven by a belt 71 and the motor 73 (FIG. 13). Means for indicating to the operator which racks have been processed and which ones have not can be associated with the conveyor 67, which becomes accessible by opening a hatch (not illustrated). For example, the various positions that are occupied by the seats 65 of the conveyor 67 can be associated with LEDs of two different colors (e.g. red and green). The lighting of one or other of the LEDs is controlled by the central unit 47 as a function of the procedures performed. For instance, all the racks still to process are identified by the red LED coming on, while all the racks already processed are identified by the green LED coming on. This enables the operator to rapidly recognize the racks that can be removed and replaced with new racks to process, without needing to check whether the test tubes (or some of them) have been removed from the racks. This also prevents any racks only containing test tubes with samples not destined for ESR measurement from accidentally being left inside the device.

Moreover, provision may also be made for the processed racks to be unloaded automatically, by extending the stroke of the transfer device 61, which can take effect to eject the processed racks through a slot provided in the cover on the device.

The transfer of the single test tubes P needing to be analyzed by the means underlying the setup unit 51 is done using the elements illustrated in detail in FIGS. 12 and 15-18. These elements are omitted from the drawings in FIGS. 13 and 14 for the sake of clarity.

Figure 15:
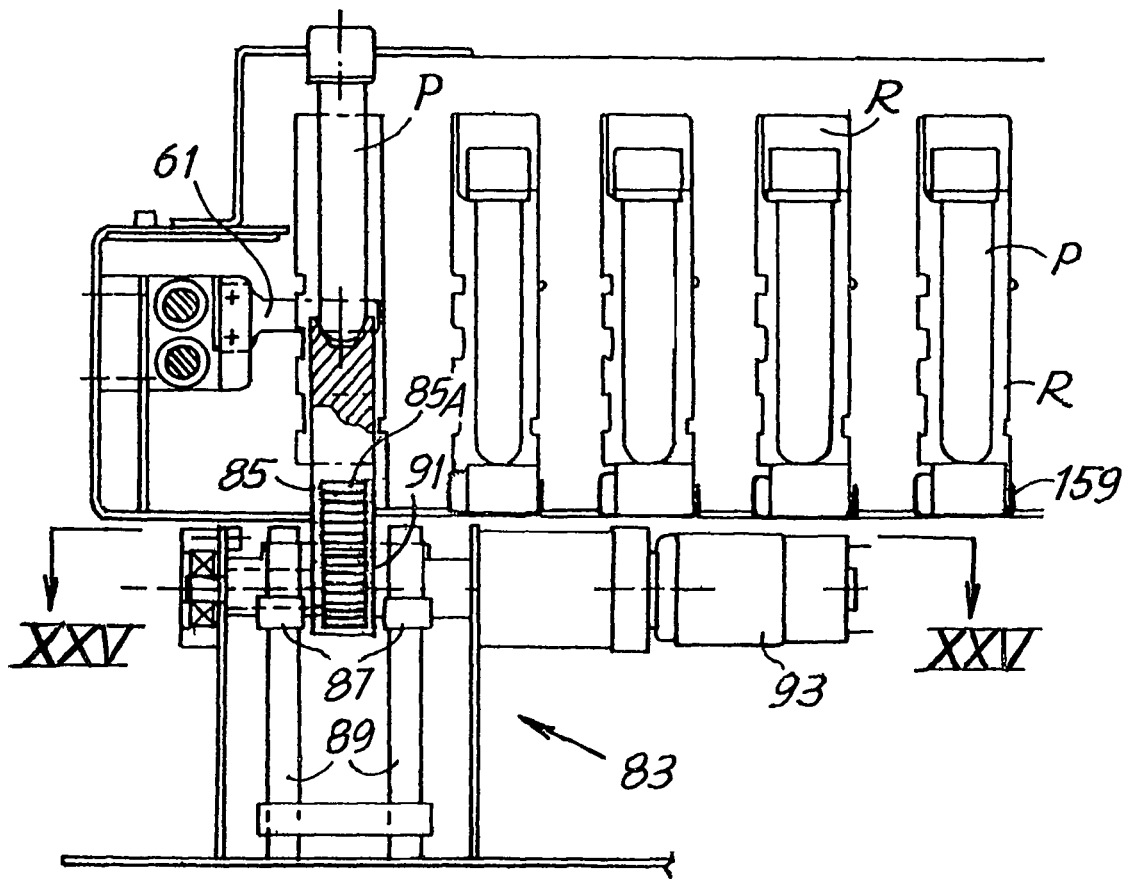
FIG. 15 shows a side view of the extractor for removing the test tubes from the racks.
Figure 16:
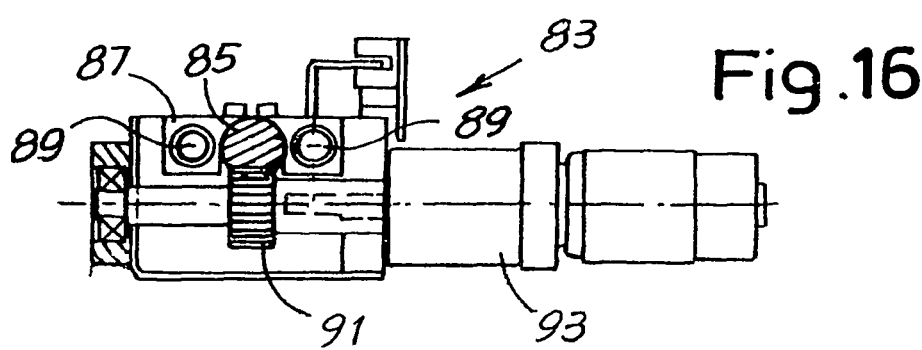
FIG. 16 shows a view along the line XVI-XVI of FIG. 15.

Under the level of the base of the single racks, downstream from the barcode reader 63, in the position indicated by the numeral 81 in FIG. 13, there is an extractor globally indicated by the numeral 83, as illustrated in detail in FIGS. 15 and 16. It has a cursor 85 solidly attached to a sliding shoe 87 that slides along vertical guides 89. The top end of the cursor 85 is shaped with a cavity for containing the bottom of the test tubes P. The cursor has gearing 85A engaging with a pinion 91 that is turned by a motor 93 interfaced with the control unit 47. When a test tube P that is in line with the cursor 85 has to be transferred to the part underneath the device, the cursor is raised into the position shown in FIG. 15 to slide the test tube P partially out of the rack R and make the top of it accessible to a pickup and transfer clamp, indicated by the numeral 93 and illustrated in FIGS. 17 and 18, as well as in FIG. 12. The opening and closing of the clamp 93 is controlled by a motor 95 carried by a boom 97. The shaft of the motor 95 is fitted with a cam 99 that induces the clamp to open, its closing being governed by a compression spring 101. The boom 97 is carried by a moving element 103 solidly attached to a threaded bush engaged on a threaded bar 105, the rotation of which is controlled by a motor 107. By means of the threaded bar 105 the motor 107 controls the up and down movement of the clamp 93 in the direction of the double arrow f93.

The motor 107 and the threaded bar 105 are carried by a bearing 109 capable of oscillating movement around a vertical axis Y-Y, driven by a motor 111, by means of a screw 13 and a sector of toothed wheel 115 solidly attached to the bearing 109.

With this arrangement, each test tube P partially removed by the extractor 83 from its rack R is picked-up by the clamp 93, which can grasp it under the plug, avoiding the risk of any test tubes accidentally being opened. Then, with a movement upwards, an oscillation around the axis Y-Y and a subsequent movement downwards, the test tube P is inserted by the clamp 93 in the seat 3C in the holder 3 currently in position A. To ensure the proper insertion of the test tube P in the seat 3C, the clamp is opened, raised, closed and then lowered again to press on the plug of the test tube until it has been inserted completely in the holder, as determined by the detection of the torque applied by the motor 107.

The test tube inserted in the seat 3C is withheld therein by means of the tabs 3D throughout the time it takes to complete the previously-described agitation, sedimentation, reading and ejection procedures. The ejectors (not illustrated) that are installed in positions E and F along the path of the flexible member 1 can be made in a manner similar to the extractor 83 of FIGS. 15 and 16, except for a greater length of the cursor 85, which will have to completely eject the test tube from the seat 3C.

A different embodiment of the invention is shown in FIGS. 19 to 27 and is described herein below.

Figure 19:
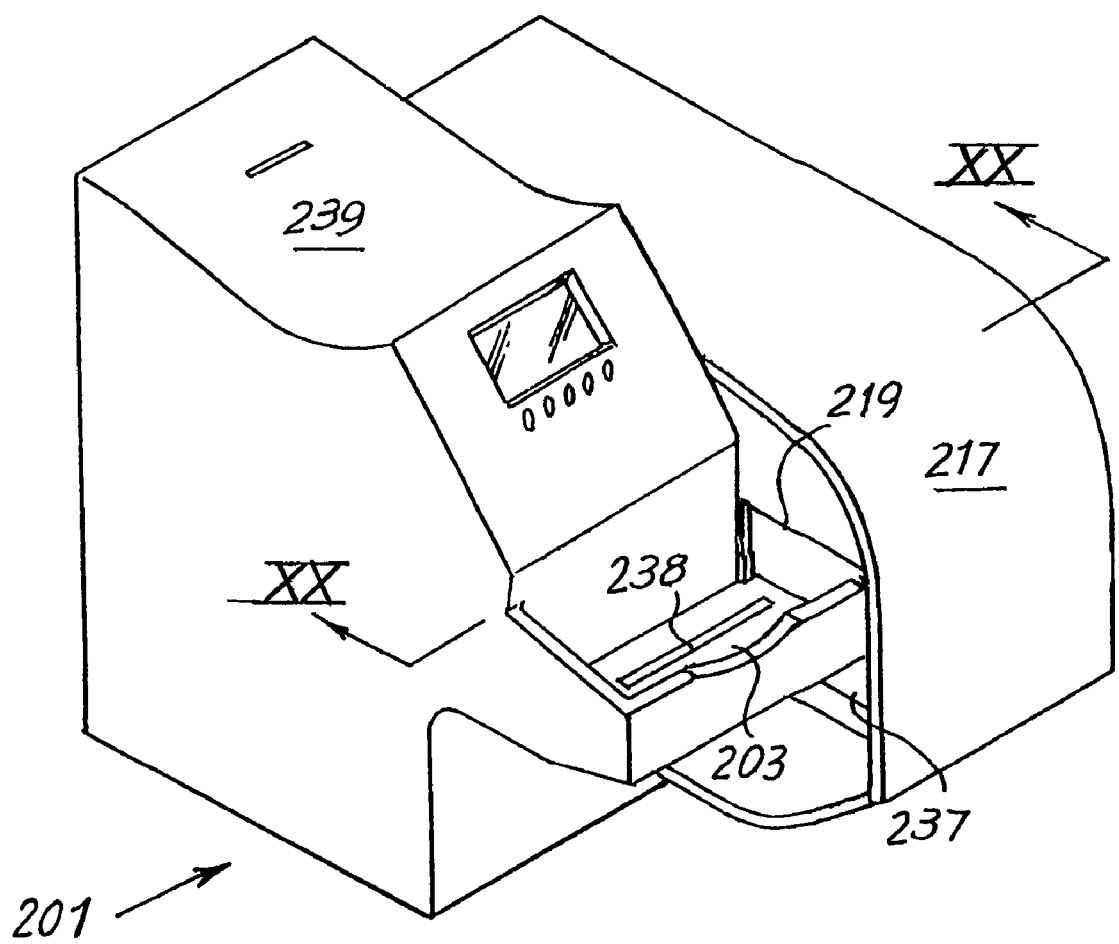
FIG. 19 is an outside axonometric view of the device according to the invention.

FIG. 19 shows an outside axonometric view of the device according to this embodiment of the invention, generically indicated by the numeral 201. The device comprises a tray for loading the racks of test tubes to analyze, indicated by the numeral 203. On the bottom of the tray 203, indicated by the numeral 203A (FIG. 20), there is a slot 203B along which there slides a plunger 205 solidly attached to a cursor 207 and moving in the direction of the double arrow f205 to load single racks of test tubes in the device. The movement of the plunger 205 is controlled by a motor 209 by means of a pair of gears 211 that turn a threaded bar 213 engaged in a nut screw 215 solidly attached to the cursor 207. When a stack of racks, labeled R, loaded with test tubes P, is placed on the tray 203, the cursor 205 lies in the position on the left of FIG. 20. The left-to-right movement of the cursor 207 and of the plunger 205 induced by the motor 209 pushes the lowermost rack on the stack to the right into an area 217 of the device, passing through a slit 219 (FIG. 19).

Figure 21:
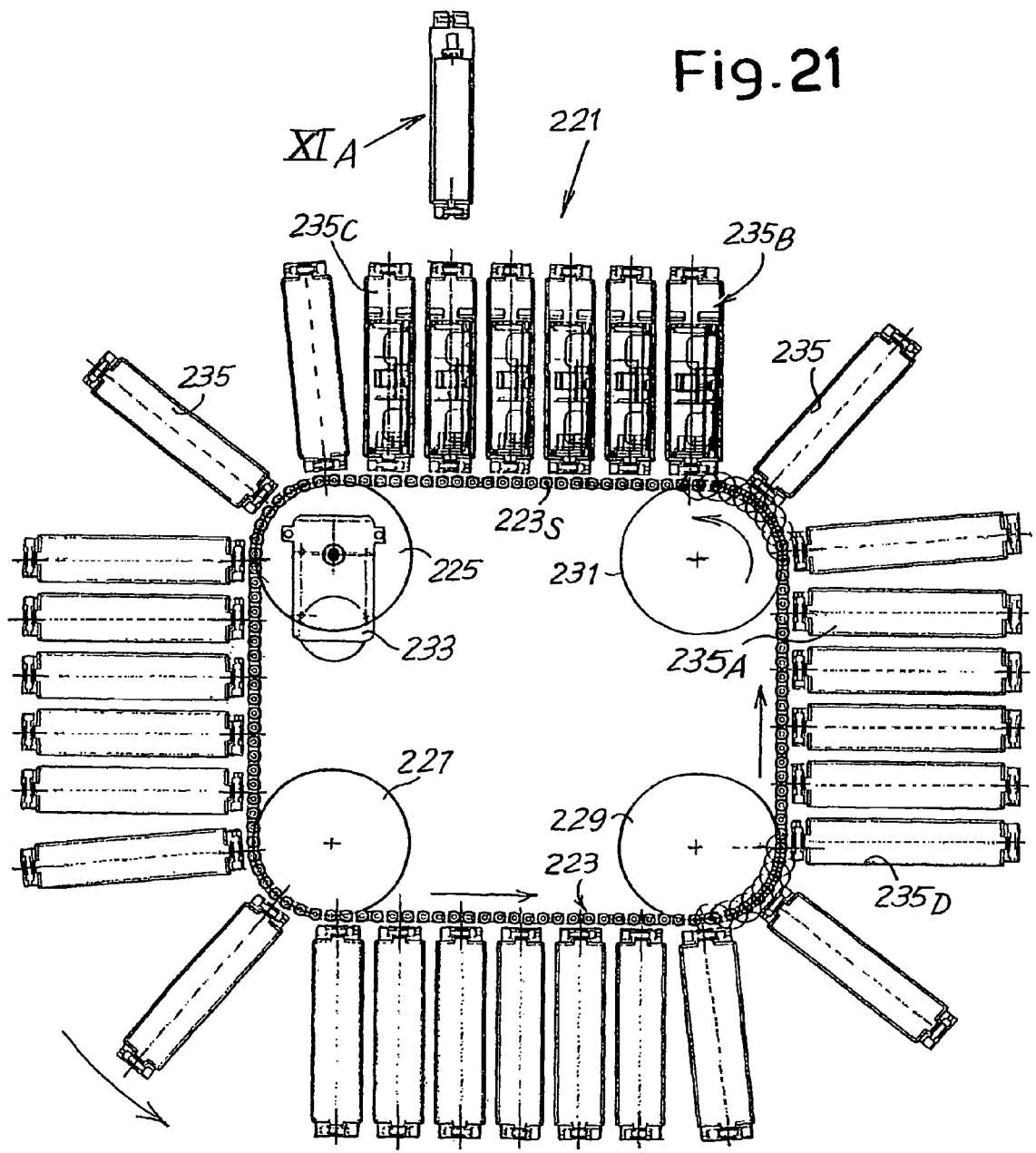
FIG. 21 is a view along the line XXI-XXI of the magazine, in a vertical plane.

Inside the area 217 of the device there is a magazine generically indicated by the numeral 221 and more readily visible in FIG. 21.

The magazine comprises a flexible element, in the example a chain 223 or a pair of chains 223, forming a continuous conveyor, driven around four toothed wheels 225, 227, 229 and 231, the wheel 225 being driven by a motor 233. Along the entire length of the conveyor 223 there are seats 235 in the shape of a double shell (see FIG. 21A). The dimension of each seat 235 is such that it can contain a rack R of test tubes. Each seat 235 is capable of enveloping, or surrounding, each rack inserted therein, so that the rack R can complete the distance covered by the conveyor 223, even along its lower stretch, without falling. As shown more in detail in FIG. 21, the path of the seats 235 covered by the conveyor 223 passes through a first loading position, indicated by the numeral 235A in said figure. The seat 235 that occupies this position is aligned with the slit 219 and receives the rack driven by the plunger 205.

Downstream from the position 235A, with respect to the direction in which the conveyor 223 advances along its path, there is a second position, indicated by the numeral 235B, from where the rack contained in the seat situated in said position is pushed, by a plunger not illustrated and of a type conceptually similar to the plunger 205, towards a sedimentation area, described later on. Downstream from the position 235B along the path of the conveyor 223 there is a third position, indicated by the numeral 235C wherein the racks that have been processed, i.e. that have already undergone the reading, are reinserted in the seat occupying said position. Said reinsertion movement can be achieved by a plunger such as the above-described plunger 205.

Finally, upstream from the position 235A there is a position 235D from where the processed racks are ejected from the device. The position 235D is aligned with a slit 237 (FIG. 19) from where the processed racks leave the device 201. Said ejection movement is achieved by a plunger not illustrated and conceptually much the same as the plunger 205.

In the position 239 of the device (FIG. 19) there is a sedimentation area wherein the racks are transferred from the magazine 221 and from where the processed racks (that have already undergone reading) are ejected and reinserted in the magazine 221.

Figure 22:
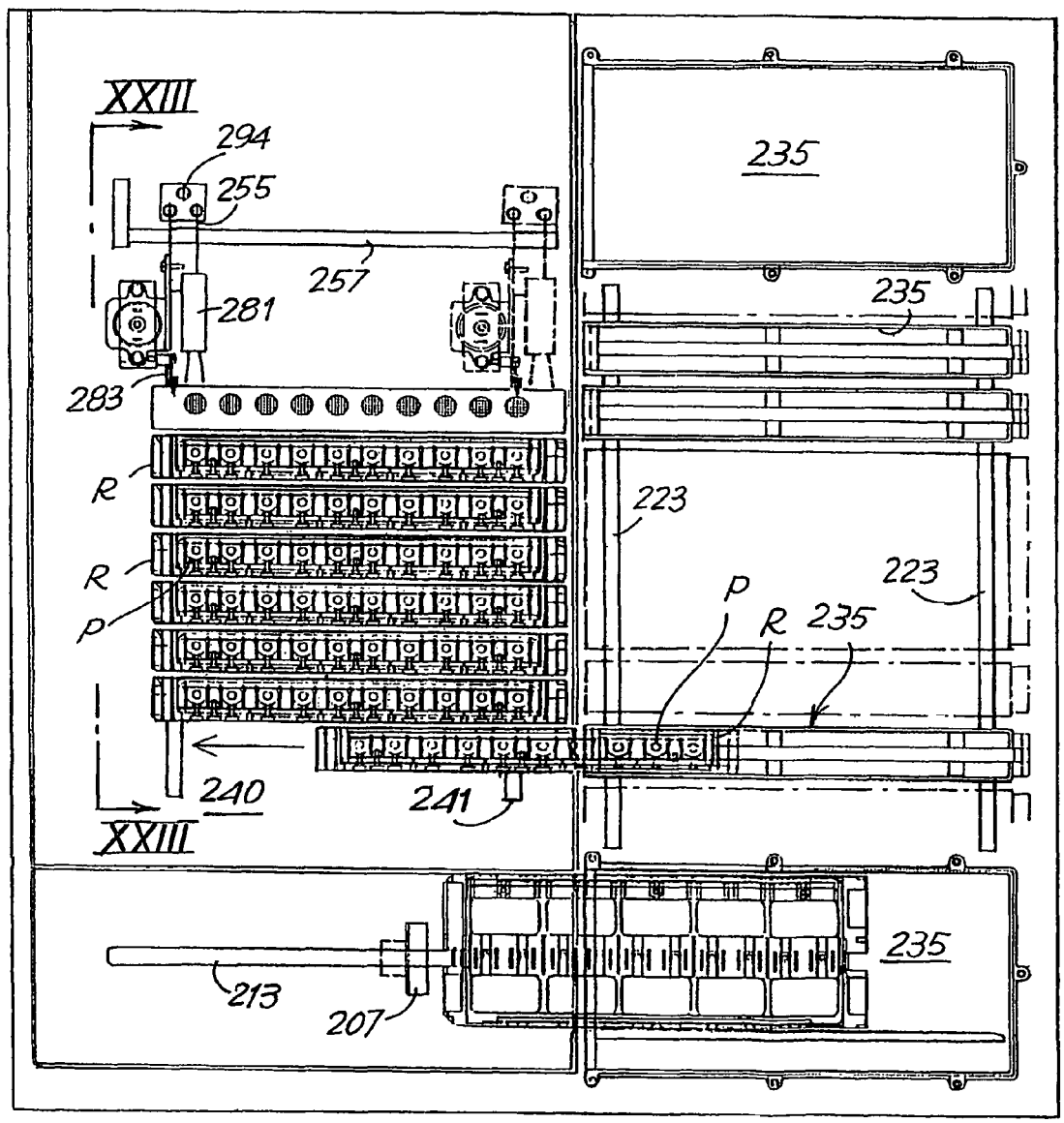
FIG. 22 is a plan of the magazine (with parts removed), of the sedimentation area and of the reading area, in a first embodiment of the invention.

The sedimentation and sample reading areas are shown in more detail in FIGS. 22 and 23, in a first embodiment.

In the sedimentation area, globally indicated by the numeral 240, there is a second flexible conveyor 241, again comprising a chain or a plurality of chains, driven between two toothed wheels 243 and 245, one of which is motorized.

Seats 247 for containing the single racks R coming from the magazine 221 are attached to the chain 241. Unlike the seats 235 in said magazine, the seats 247 do not surround the racks, they simply support them. As will become clear from the following explanation, the racks are only kept on the conveyor 241 along the upper horizontal stretch of the conveyor, indicated by the numeral 241S in FIG. 23, which lies substantially at the same height as the upper stretch 223S of the chain 223 of the magazine 221. The two stretches 241S and 223S are substantially parallel to each other. This arrangement enables the direct transfer of the racks from one of the conveyors 223 and 241 to the other by means of plungers similar to the one indicated by the numeral 205 and illustrated for the insertion of the racks in the device. These further plungers for transferring the racks between the conveyors 223 and 241 are not illustrated in the drawing for the sake of simplicity.

Each rack inserted in a respective seat 247 of the conveyor 241 is transferred from an insertion position 247A (see FIG. 23) to a reading position 247B in a reading area generically indicated by the numeral 248. The time the test tubes spend in the sedimentation area, represented in practical terms by the upper stretch 241S of the conveyor 241, equates to the sedimentation time specified by the protocols for measuring the ESR. The number of seats 247 that come to be along the stretch 241S of the conveyor 241 and the time it takes to transfer the single racks from the position 247A to the position 247B also depends on the number of test tubes each rack can contain, since said number determines the time it takes to complete the reading of all the test tubes in a given rack.

Various devices can be provided in the reading area 248 to read the samples, depending on the design of the device. The attached drawing shows two different possible configurations of these reading means.

Figure 26:
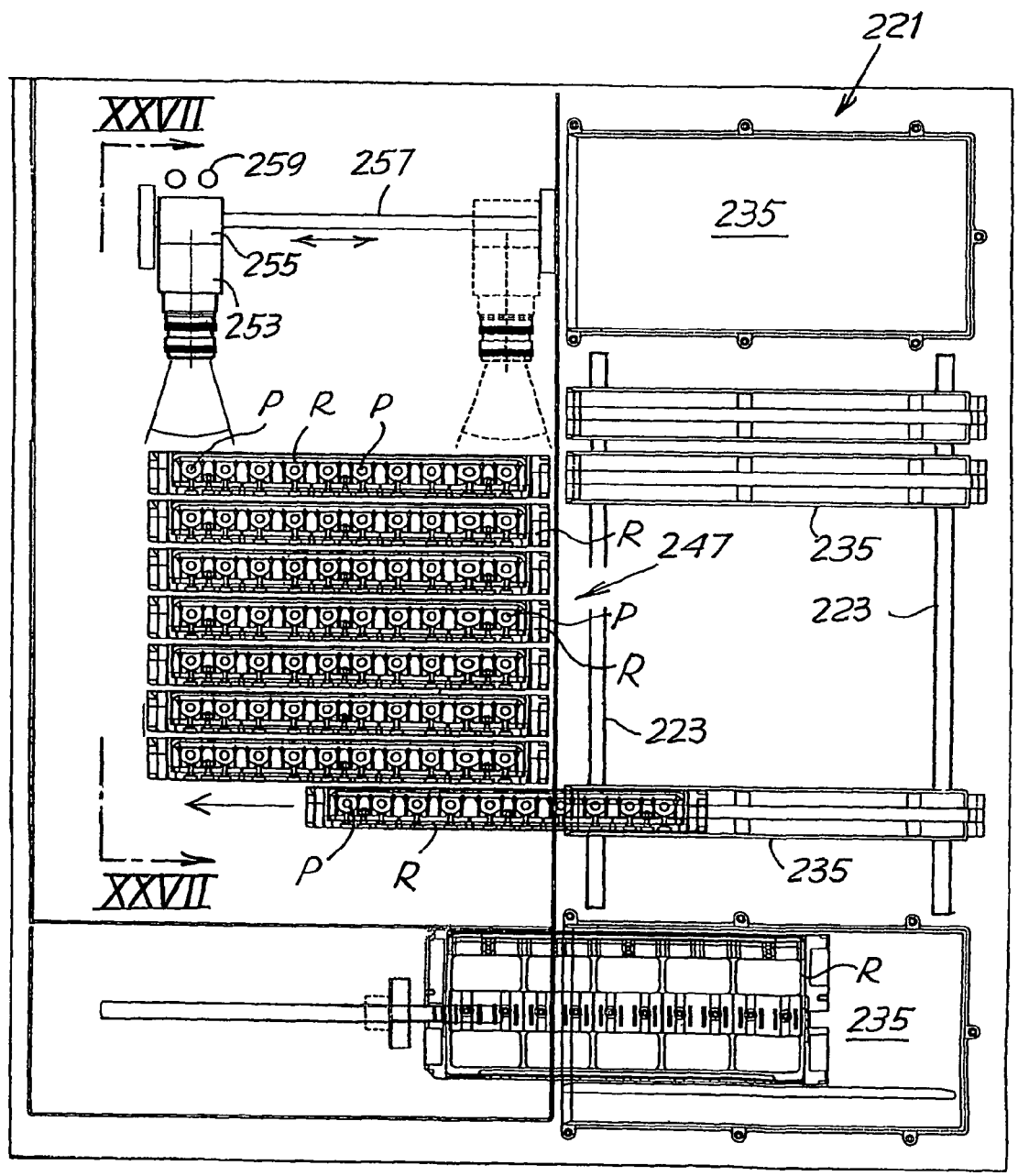
FIG. 26 is a plan (with parts removed) similar to the view of FIG. 22, in a different embodiment.
Figure 27:
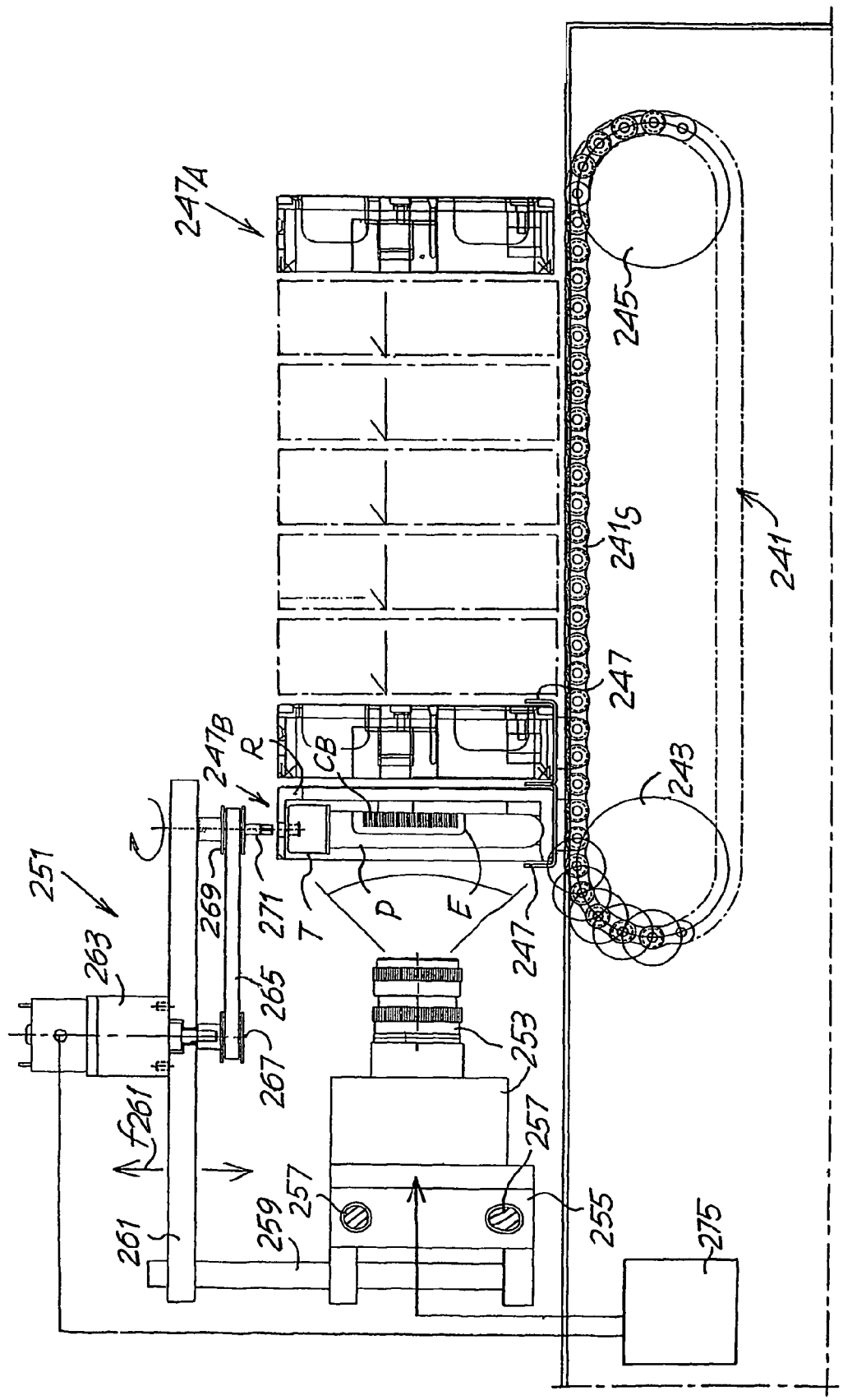
FIG. 27 is a view along the line XXVII-XXVII of FIG. 26.

Referring initially to FIGS. 26 and 27, in a first embodiment, there is a video camera 253 in the reading area 251, mounted on a slide 255 that is movable in the direction of the double arrow f255 along fixed horizontal guides 257. Said guides 257 extend parallel to the racks R that are in the sedimentation and reading area. The stepping translation of the slide 255 along the guides 257 enables the video camera 253 to be brought in front of each of the test tubes P contained in the rack R in position 247B.

Vertical guide bars 259 are solidly attached to the slide 255, along which a mobile saddle 261 slides in the direction of the double arrow f261. The saddle 261 carries a motor 263 that, by means of a belt 265 and pulleys 267, 269, turns a shaped stud 271 that can fit into a cavity in the plugs T in the single test tubes P contained in the racks R. The rotation of the stud 271, that can engage and disengage the seat of the plugs T thanks to the movement of the saddle 261 in the direction of the double arrow f261, serves (as explained in greater detail later on) to correctly orient each test tube P to implement the various stages of the ESP, measurement.

The various drives and the reading system represented by the video camera 253 are interfaced with a control unit 275 that is only schematically illustrated.

Figure 20:
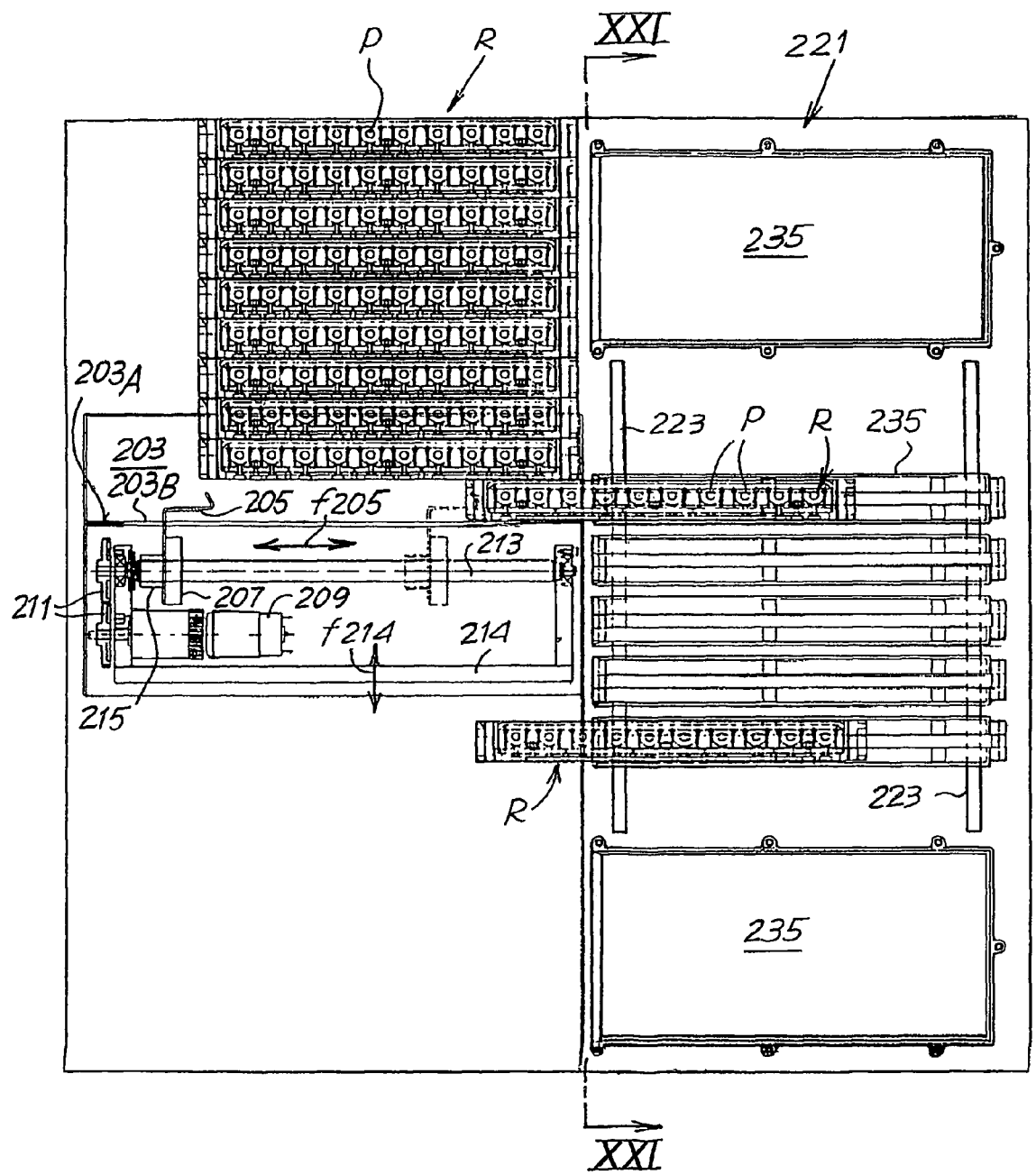
FIG. 20 is a front cross section of the device along the line XX-XX of FIG. 19.

The above-described device works as follows. A stack of racks R is placed on the surface 203A of the tray 203 (FIG. 20). The various racks R are loaded in the magazine 221 by subsequent strokes of the plunger 205. To enable the plunger 205 to complete its return stroke without interfering with the racks above it, the whole assembly 205-213 is carried by a moving element 214 which moves vertically in the direction of the double arrow f214 (FIG. 20), so that the plunger 205 can withdraw from the surface 203A when it has to return after pushing a single rack into its respective seat 235 in position 235A of the magazine 221.

With successive loading operations, all or some of the seats 235 in the magazine 221 are progressively loaded as they transit in front of the loading position 235A coinciding with the slit 219 (FIG. 79). Having loaded all the racks, on which the analyses are to be performed, the magazine 221 is moved at a rate suitable for inducing the agitation of the samples contained in the single test tubes P in each rack R. The motion of the magazine, induced by the motorized wheel 225 acting on the chain 223, continues for a time long enough to obtain a sufficient agitation of some or all of the samples, i.e. those contained in the racks that are the first to be transferred to the sedimentation area. When the racks have to be transferred to said area, a plunger (not illustrated) picks up each rack occupying the position 235B and transfers it to the seat 247 occupying the position 247A in the sedimentation area. All the seats 247 occupying the upper stretch 241S of the conveyor 241 are filled with successive steps of the conveyor 223 and of the conveyor 241. Then the reading of the test tubes P contained in the racks R in the position 247B, i.e. in the rack that was loaded first, can begin. If the time that has elapsed between the loading of the rack in the sedimentation area and the moment when this comes into the reading area does not coincide with the time needed for sedimentation, the device can then keep the container 241 at rest for the time it takes to complete the sedimentation of the samples.

The reading begins with the positioning of the video camera 253 in one or other of the two end positions. In the example illustrated (FIG. 26), the video camera is in the left-hand position and thus begins to read the test tubes starting from the test tube furthest to the left contained in the rack R in position 247B. The test tube P can be a dedicated test tube for ESR analyses or a generic test tube, i.e. a test tube for CBC. Usually all the test tubes P that are in a given rack will be of the same type and preferably all the racks in the same processing batch will contain test tubes of the same type. This means 5 that all the test tubes contained in the device will generally be of the type specifically for measuring the ESR or of the type for CBC. Using a data-processing software resident in the unit 275, the video camera 253 can recognize every type of test tube P in front of which it is positioned in each case. So, generally speaking, test tubes of different types can also be mixed together inside the same rack, since the device is capable of recognizing the type of test tube that is presented in front of the video camera each time.

The recognition of the type of test tube may be important when (as is usually the case) the anticoagulant provided in the test tubes for a CBC is not the same as the one used in the test tubes for the ESR. By means of the control unit 275 and the video camera 253, the device is capable of recognizing the type of test tube and thus of establishing whether a correction algorithm must be applied to the ESR measurement, as in the case of the anticoagulant type K3EDTA being used, or whether the measurement can be recorded without applying any correction algorithm. It may also be that the set-up of the appliance is done manually, by means of a user interface, especially when the test tubes in a given batch to process are all the same.

Instead of using image-processing, the type of test tube P can also be recognized, for instance, by reading the information contained in a transponder associated with a given rack R coming into the reading area. In this case, there will also be an aerial in the reading area for reading the content of the transponder inside the rack.

The label with the bar code or other machine-readable code, attached to the test tube, must be read before taking the ESR reading on a given test tube P in front of the video camera 253. Said label is indicated by the letter E in FIG. 27, while CB identifies the bar code printed on said label. The label E can be attached to the body of the test tube (as is usually the case with test tubes for CBC) or on the neck near the plug T in said test tube (as is often the case with test tubes specifically for measuring the ESR), or on test-tube appendages provided specifically for said purpose.

The bar code CB contains information that enables the single sample inside the test tube to be correlated with a given patient to whom the sample belongs. This enables the device to send the analytical data resulting from the analysis, together with the patient's data, to a data processor to which it is connected. The bar code also contains information relating to the type of analyses to perform on the sample contained in the test tube. In fact, it may be that a given test tube has to undergo different tests from adjacent test tubes. It may also be that a specific test tube P does not need to undergo the ESR measurement, in which case the device 201 is capable of skipping the reading of the test tube containing the sample on which no ESR measurement is required.

To read the information contained in the bar code CB, the test tube P must be oriented so as to present the label E in front of the video camera 253. Although the correct orientation of the test tubes for said purpose can be done by the laboratory personnel, according to the herein-illustrated preferred embodiment of this device according to the invention, the reading area 251 houses the system 261-271 for performing the angular orientation of the test tube around its own axis and bringing the label E into position for reading. Thus, after positioning the video camera 253 in front of the first test tube P of the rack R in the reading position, the saddle 261 is lowered until the stud 271 engages inside the respective seat in the plug T in the test tube P. The stud 271 is turned by the motor 263 until the video camera 253 "sees" the label E within its visual field. Then the rotation can be interrupted and the video camera reads the information contained in the bar code CB with the aid of the image-processing software.

If the test tube being examined contains a sample that has to undergo an ESR measurement, the video camera proceeds to read the content of the test tube. To do so, the obstacle presented by the label E previously brought in front of the video camera must first be removed. For this purpose, the motor 263 is started again, and it turns the test tube P again around its own axis in order to bring the label E around to the side of the test tube furthest away from the video camera 253. The video camera can thus see the content of the test tube (through the slot provided in the rack R, which also allows for the reading of the label E) and check the height at which the separation occurs between the sediment inside the test tube and the serum. As well known, this height gives the measure of the erythrocyte sedimentation rate, deriving from the sedimentation time (fixed for all samples) and from the height at which the above-mentioned separation occurs with respect to the total height of the sample.

Based on the image of the inside of the test tube P captured by the video camera 253, the image-processing software resident in the unit 275 determines the erythrocyte sedimentation rate for the single sample P. When the test tube P is a test tube for CBC, the calculation also takes the nature of the anticoagulant into account and the unit 275 applies the correlation algorithm to implement the calculation.

After completing these procedures, the saddle 261 having been raised previously to disengage the stud 271 from the plug T in the test tube P, the slide 255 is transferred in stepping mode to present the video camera 253 in front of the adjacent test tube and thus repeat the above procedures on the next tube.

These procedures are completed for all the test tubes contained in the rack R in position 247B, until the video camera 253 comes to the last test tube in the rack being processed.

After completing the reading of the test tubes in the rack R in position 247B, said rack is again pushed (by a plunger not illustrated) into the seat 235 on the conveyor 223 that is in position 235C (see FIG. 21).

The conveyor 241 then advances a step to bring the next rack into position for reading and an empty seat 247 in position 247A, where the next rack (if any) coming from position 235B of the magazine 221 will be inserted by the plunger provided (not illustrated).

As soon as a processed rack comes into position 235B, it is ejected by a specific plunger through the aforementioned slit 237.

The above is a description of a device that uses a video camera and image-processing software to take all the readings, both of the information contained on the label attached to the single test tubes, and of the level of the sediment inside each test tube. In this embodiment, the video camera can also be used (as mentioned earlier) to recognize of the type of test tube used to contain the sample.

This is not the only feasible solution, however. The systems for reading both the information on the labels and the content of the test tubes may also be of other kinds.

A different solution is illustrated in FIGS. 22 to 25, which also show details of the drive motors, that can be used in the embodiment of FIGS. 26 and 27 too, but were omitted in the latter case for the sake of simplicity of representation.

In the embodiment of FIGS. 22 to 25, the video camera 253 is replaced by a bar code reader indicated by the numeral 281 and a capacitive sensor indicated by the numeral 283. The bar code reader 281 is mounted on a slide or saddle, again indicated by the numeral 255, equivalent to the slide 255 carrying the video camera 253 and moving along horizontal guides 257. The slide 255 with the bar code reader 281 is moved along the guides 257 in the direction of the double arrow f255 by a threaded-bar control, not illustrated. The capacitive sensor 283 is capable of an up and down movement in the direction of the double arrow f283, said movement being controlled by a motor 285 carried by the slide 255. The movement is guided by vertical guide bars 286, with a threaded bar 288 between them, turned by the motor 285 on which a nut screw 290, solidly attached to the capacitive sensor 283, engages. The guide bars 286, the threaded bar 288 and the motor 285 are carried by a shaped profile 292 forming part of the slide 255, or solidly attached thereto.

As in the previous embodiment, here again there are vertical bars or guides 259 solidly attached to the slide 255 that carry a saddle 261 with a motor 263 for driving the rotation of a stud 271 via the transmission 265, 267, 269. The up and down movement of the saddle 261 is controlled by a threaded bar 294 that engages in a nut screw 296 solidly attached to the slide 255. The threaded bar 294 is turned by a motor 298 supported by the saddle 261 (see also FIG. 24).

The operation of the device equipped with the reading system illustrated in FIGS. 22 to 25 is much the same as in the embodiment previously illustrated with reference to FIGS. 26 and 27, except for the different method for reading the information and code on the label E of the test tube P. In this case, in fact, the bar code reader 281 is only used to read the information printed in bar 5 code format on the label E attached to the test tube P or its plug T. The rotating stud 271 is again used to correctly orient the test tube P angularly around its own axis to enable its reading. The extension in height of the bar code reader 281 is sufficient to read the label, whatever position it is in along the length of the test tube P and its plug T.

After reading the content of the label E, the capacitive sensor 283 slides vertically in the direction of the arrow f283 from the top downwards or, vice versa, from the bottom upwards, and reads the content of the test tube, identifying the separation zone between the part occupied by the plasma and the part occupied by the sediment in the sample contained in said test tube. The nature of the capacitive sensor makes it unnecessary to turn the test tube again to move the label E outside the area being read by said sensor, whereas said rotation is essential in the case of using a video camera.

In this case, since there is no video camera and respective image-processing software, the recognition of the type of test tube P must be done differently from the situation described with reference to FIGS. 26 and 27 in order to establish which procedure to use to calculate the erythrocyte sedimentation rate. For this purpose, a transponder associated with the rack and a respective reader situated in the reading area can be used. Here again, as already mentioned previously, it may also be that the operator manually specifies the type of test tube used d all the test tubes in the various racks of a given batch are of the same type.

Interpreting the code on the test tube, for instance a bar code, can also tell the system about the type of container involved.

From the above description, it is clear that the invention enables the drawbacks of conventional methods and devices to be overcome, by allowing for a reading of the ESR to be taken on any type of test tube, even of the type used for CBC, without needing to draw the sample from the test tube in question and without having to remove the sample from the rack that contains it.

While specific embodiments of the invention have been shown and described in detail to illustrate the application of the principles of the invention, it will be understood that the invention may be embodied otherwise without departing from such principles.

The invention claimed is:

1. An erytrocyte sedimentation rate measuring device for blood samples, the device comprising:
   holders for test tubes containing samples of biological fluids;
   agitator devices for agitating said test tubes;
   at least a first detector and a second detector for detecting the levels inside said test tubes;
   a control unit, wherein said holders are formed in a continuous flexible member defining a closed path, said agitator devices, said first detector and said second detector being arranged in sequence along said path, said first detector being located at a spaced location from said second detector via a sedimentation area, said control unit determining the erythrocyte sedimentation rate based on levels inside said test tubes detected by said first detector and said second detector.

2. A device as in claim 1, wherein said agitator devices are arranged and said agitator devices oscillate said holders such that fluid in said holders is stirred.

3. A device as in claim 1, wherein the following are arranged along said closed path:
   at least one agitating area, wherein said agitator devices are provided, said sedimentation area being located along said closed path; and
   at least one reading area wherein one of said first detector and said second detector is installed.

4. A device as in claim 1, wherein said flexible member defines a path lying on a substantially horizontal plane.

5. A device as in claim 1, wherein said holders comprise elements interconnected to form a flexible chain member.

6. A device as in claim 5, wherein each of said elements comprises a single seat for a respective test tube.

7. A device as in claim 5, wherein the elements forming said flexible member are connected together by means of couplings, said flexible member moving in a traveling direction, each of said holders being mounted for movement such that each of said holders is rotatable with respect to an adjacent holder about a horizontal axis, said horizontal axis being parallel to said traveling direction, wherein one or more of said holders rotate about said horizontal axis via at least one of said agitator devices, whereby fluid in said one or more of said holders is stirred via said at least one of said agitator devices.

8. A device as in claim 7, wherein said couplings are composed of spherical joints.

9. A device as in claim 4, wherein said agitator devices oscillate said elements forming the flexible chain member such that at least one of said holders rotates about a horizontal axis defined by said continuous flexible member.

10. A device as in claim 9, wherein said agitator devices comprise guides, said elements engaging said guides such that said at least one of said holders rotates about said horizontal axis via said guides.

11. A device as in claim 10, wherein said elements have sliding shoes engaging in said guides.

12. A device as in claim 9, wherein said agitator devices comprise mobile guides, said mobile guides extending along a portion of the path covered by said flexible member, wherein said elements forming the flexible member are engaged, said guides being mounted for movement such that said guides rotate said at least one holder about said horizontal axis, wherein fluid in said at least one holder is mixed via rotation of said at least one holder.

13. A device as in claim 9, wherein said agitator devices comprise a rotor coaxial to a portion of the path of said flexible member and provided with engaging elements for engaging the holders that come to be along said portion along the path of the flexible member, said rotor being mounted for movement such that said rotor rotates or oscillates about an axis thereof.

14. A device as in claim 13, wherein said engaging elements are in the form of guides within which said holders forming the continuous flexible member are slidingly engaged.

15. A device as in claim 1, wherein said first detector is arranged along said closed path, downstream from the agitator devices, and said second detector is arranged further along said path, downstream from a portion of path defining said sedimentation area.

16. A device as in claim 15, further comprising:
   a third detector arranged along said path, downstream from a further portion of path defining a second sedimentation area.

17. A device as in claim 5, wherein said continuous flexible member comprises a transponder associated with each test-tube holder.

18. A device as in claim 5, wherein each of said elements is associated with a respective transponder.

19. A device as in claim 17, wherein along said path there are one or more stations for scanning said transponders.

20. A device as in claim 1, wherein along said closed path there is at least one extractor, for removing the test tubes from said holders.

21. A device as in claim 20, wherein along said closed path there are two extractors for removing the test tubes from said holders and distributing them in respective containers.

22. A device as in claim 1, further comprising automatic manipulators are provided for automatically inserting the test tubes in said holders.

23. A device as in claim 22, wherein said manipulators are move single test tubes from a rack of test tubes and insert said test tubes in said holders.

24. A device as in claim 1, further comprising a setup unit for preparing the test tubes for insertion in said holders.

25. A device as in claim 24, wherein said setup unit is situated above said continuous flexible member.

26. A device as in claim 24, wherein said setup unit comprises a reading station for automatically reading labels attached to said test tubes, to ascertain in each case whether said test tubes must undergo a measurement of the sedimentation rate of the sample contained therein.

27. A device as in claim 23, wherein said manipulators are controlled and operated by a central unit as a function of information provided for each test tube by reading stations, to transfer the test tubes in which the sedimentation rate must be measured from the rack to a corresponding holder.

28. A device as in claim 24, wherein said setup unit comprises at least one first conveyor for moving a plurality of racks containing test tubes with samples of biological fluid to analyze.

29. A device as in claim 28, wherein said setup unit comprises a first transfer unit for removing single racks from said first conveyor and transferring said single racks to said reading station.

30. A device as in claim 23, wherein said manipulators include a lower push bar, said lower push bar engaging the test tubes contained in the racks such that said test tubes slide partially out of said racks, and said manipulators comprise a mobile clamp for removing the test tubes from the respective racks and inserting said test tubes in corresponding holders in the continuous flexible member.

31. A device as in claim 28, wherein said setup unit includes a second conveyor for moving a plurality of racks and a second transfer device for transferring the racks from the second conveyor to the first conveyor.

32. A device as in claim 31, wherein the first transfer device transfers the racks from the first conveyor to the reading station and from said reading station to the second conveyor.

33. A device as in claim 28, further comprising means for identifying the status of each rack associated with one or more of said first and second conveyors of said setup unit.

34. A device in accordance with claim 2, wherein along said closed path are arranged said sedimentation area, at least one agitating area, wherein said agitator devices are provided, and at least one reading area wherein one of said first detector and said second detector is installed.

35. A device in accordance with claim 2, wherein said flexible member defines a path lying on a substantially horizontal plane.

36. A device in accordance with claim 3, wherein said flexible member defines a path lying on a substantially horizontal plane.

37. A device in accordance with claim 1, wherein said holders comprise elements interconnected to form a flexible chain member.

38. A device in accordance with claim 34, wherein along said path, two readings are taken on biological samples in each test tube, the first reading when the test tube leaves the agitation area and second reading at end of the sedimentation area.

39. A device as claimed in claim 1, wherein:
said continuous flexible member comprises elements connected to one another via couplings, wherein consecutive elements are movable with respect to one another about an axis substantially parallel to a travel direction of said continuous flexible member via said couplings such that each of said elements is rotatable about said axis via at least one of said agitator devices; and
each element comprises at least one seat for one of the test tubes, said at least one of said agitator devices rotating one or more of said elements about said axis such that blood samples contained in said test tubes are mixed via rotation of said elements.

40. A device according to claim 39, wherein said agitation device comprises a rotor and guides, said rotor being mounted for movement such that said rotor rotates about said axis, wherein consecutive elements move along said guides and across said rotor when said elements are advanced along said path, whereby said consecutive elements engage said guides, said rotor rotating said elements and the test tubes held by said seats about said axis.

41. An erythrocyte sedimentation rate measuring device for blood samples, the device comprising:
a plurality of test tubes, each of said test tubes comprising samples of biological fluids;
a plurality of holders, one of said test tubes being inserted into at least one of said holders, each of said holders being connected to an adjacent holder to define an endless flexible member, said endless flexible member being movable along a closed path, each of said holders being rotatable about a horizontal axis with respect to said adjacent holder;
a plurality of agitator devices, at least one of said agitator devices receiving one or more of said holders such that said one or more of said holders is rotated about said horizontal axis, wherein said biological fluids in said one or more of said holders is mixed via rotation of said holders;
a first detector;
a second detector;
a control unit, said agitator devices, said first detector and said second detector being arranged along said closed path, said first detector being arranged adjacent to at least one of said agitator devices, said second detector being disposed downstream of said first detector and said agitator devices, wherein a portion of said endless flexible member extending between said first detector and said second detector defines a sedimentation area, said first detector detecting a first level of said biological fluids in said one or more holders after said one or more holders are rotated by said agitator devices, said second detector detecting a second level of said biological fluids in said one or more holders after said one or more holders are moved along said sedimentation area, said control unit determining an erythrocyte sedimentation rate based on said first level and said second level of said biological fluids.

42. A device according to claim 41, wherein said at least one of said agitator devices rotates said one or more holders from between a first position and a second position, said one or more holders being in a substantially vertical position in said first position, said one or more holders being in a non-vertical position in said second position.

43. A device as in claim 41, wherein said holders via coupling elements, said flexible member moving in a traveling direction, wherein one or more of said holders rotate about said horizontal axis via said coupling elements.

44. An erythrocyte sedimentation rate measuring device for blood samples, the device comprising:
a plurality of test tubes, each of said test tubes comprising samples of biological fluids;
a plurality of holders, one of said test tubes being inserted into at least one of said holders, each of said holders being connected to an adjacent holder to define an endless flexible member, said endless flexible member being movable along a closed path, each of said holders being rotatable about a horizontal axis with respect to said adjacent holder;

a holder rotating means for receiving one or more of said holders and rotating said one or more of said holders about said horizontal axis such that the biological fluids in said test tubes are mixed via rotation of said holders;

a first detector;

a second detector;

a control unit, said holder rotating means, said first detector and said second detector being arranged along said closed path, said first detector being arranged adjacent to said holder rotating means, said second detector being disposed downstream of said first detector, wherein a portion of said endless flexible member extends between said first detector and said second detector, said portion of said endless flexible member defining a sedimentation area, said first detector detecting a first level of said biological fluids in said one or more holders after said one or more holders are rotated by said holder rotating means, said one or more holders being moved along said sedimentation area after being detected by said first detector, said second detector detecting a second level of said biological fluids in said one or more holders after said one or more holders are moved along said sedimentation area, said control unit determining an erythrocyte sedimentation rate based on said first level and said second level of said biological fluids.

45. A device according to claim 44, wherein said holder rotating means rotates said one or more holders from between a first position and a second position, said one or more holders being in a substantially vertical position in said first position, said one or more holders being in a non-vertical position in said second position.

\* \* \* \* \*